(12) United States Patent
Nejhad et al.

(10) Patent No.: US 7,658,870 B2
(45) Date of Patent: Feb. 9, 2010

(54) POLYMER MATRIX COMPOSITES WITH NANO-SCALE REINFORCEMENTS

(75) Inventors: Mohammad Naghi Ghasemi Nejhad, Honolulu, HI (US); Vinod P. Veedu, Honolulu, HI (US); Andrea Yuen, Honolulu, HI (US); Davood Askari, Honolulu, HI (US)

(73) Assignee: University of Hawaii, Honolulu, HI (US)

( * ) Notice: Subject to any disclaimer, the term of this patent is extended or adjusted under 35 U.S.C. 154(b) by 407 days.

(21) Appl. No.: 11/524,091

(22) Filed: Sep. 20, 2006

(65) Prior Publication Data

US 2007/0142548 A1 Jun. 21, 2007

Related U.S. Application Data

(60) Provisional application No. 60/753,006, filed on Dec. 21, 2005, provisional application No. 60/753,155, filed on Dec. 20, 2005, provisional application No. 60/753,496, filed on Dec. 22, 2005.

(51) Int. Cl.
  *H01B 1/20* (2006.01)
  *H01B 1/24* (2006.01)
  *C09G 1/16* (2006.01)
  *A61Q 3/02* (2006.01)

(52) U.S. Cl. .............. 252/511; 252/519.33; 132/73; 106/3; 424/486; 424/487

(58) Field of Classification Search ............. 252/510, 252/511, 519.3, 519.33, 519.5; 424/484, 424/485, 486, 487, 489, 401; 106/400, 409, 106/425, 428, 429, 430, 431, 436, 437, 472, 106/476, 482, 499, 500, 3, 6; 132/200, 73; 977/926

See application file for complete search history.

(56) References Cited

U.S. PATENT DOCUMENTS

| | | | |
|---|---|---|---|
| 6,495,258 B1 | 12/2002 | Chen et al. | |
| 6,716,919 B2 | 4/2004 | Lichtenhan et al. | |
| 6,734,262 B2 | 5/2004 | Patel | |
| 6,798,127 B2 | 9/2004 | Mao et al. | |
| 6,855,202 B2 | 2/2005 | Alivisatos et al. | |
| 6,936,653 B2 | 8/2005 | McElrath et al. | |
| 7,001,556 B1 | 2/2006 | Shambaugh | |
| 7,040,948 B2 | 5/2006 | Mao et al. | |
| 7,066,978 B2 | 6/2006 | Waki et al. | |
| 7,067,096 B2 | 6/2006 | Iijima et al. | |
| 7,071,287 B2 | 7/2006 | Rhine et al. | |
| 7,071,406 B2 | 7/2006 | Smalley et al. | |
| 2002/0052434 A1 | 5/2002 | Lichtenhan et al. | |
| 2003/0064086 A1* | 4/2003 | Carrion et al. | 424/401 |
| 2003/0145779 A1 | 8/2003 | Alivisatos et al. | |
| 2003/0148042 A1 | 8/2003 | Wang | |
| 2003/0149154 A1 | 8/2003 | Heinemann et al. | |
| 2003/0203979 A1* | 10/2003 | O'Brien et al. | 516/77 |
| 2004/0029706 A1 | 2/2004 | Barrera et al. | |
| 2004/0039096 A1 | 2/2004 | Patel | |
| 2004/0063817 A1* | 4/2004 | Ilenda et al. | 523/220 |
| 2004/0067364 A1 | 4/2004 | Ishikawa et al. | |
| 2004/0070326 A1 | 4/2004 | Mao et al. | |
| 2004/0096388 A1 | 5/2004 | Ogale et al. | |
| 2004/0127621 A1 | 7/2004 | Drzal et al. | |
| 2004/0136894 A1 | 7/2004 | Yoshizawa et al. | |
| 2005/0001528 A1 | 1/2005 | Mao et al. | |
| 2005/0036933 A1 | 2/2005 | Moy et al. | |
| 2005/0040371 A1 | 2/2005 | Watanabe et al. | |
| 2005/0056118 A1 | 3/2005 | Xia et al. | |
| 2005/0084607 A1 | 4/2005 | Wang | |
| 2005/0087726 A1 | 4/2005 | Anazawa et al. | |
| 2005/0109211 A1 | 5/2005 | Shiraishi et al. | |
| 2005/0109269 A1 | 5/2005 | Alivisatos et al. | |
| 2005/0119371 A1 | 6/2005 | Drzal et al. | |
| 2005/0127030 A1 | 6/2005 | Watanabe et al. | |
| 2005/0131163 A1 | 6/2005 | Rhine et al. | |
| 2005/0220730 A1 | 10/2005 | Malnou et al. | |
| 2005/0221085 A1 | 10/2005 | Lo et al. | |
| 2005/0228099 A1 | 10/2005 | Bringley et al. | |
| 2005/0229328 A1 | 10/2005 | Tran | |
| 2005/0257715 A1* | 11/2005 | Dumousseaux | 106/400 |

(Continued)

FOREIGN PATENT DOCUMENTS

WO    WO 03/020226    3/2003

OTHER PUBLICATIONS

L. Lopez, B.M.K. Song, and H.T. Hahn, "The Effect of Particle Size in Alumina Composites", in the Proceedings of the 14th International Conference on Composite Materials (ICCM-14), San Diego, CA, Jul. 14-18, 2003, pp. 1-12.*

(Continued)

*Primary Examiner*—Douglas McGinty
(74) *Attorney, Agent, or Firm*—Knobbe, Martens, Olson & Bear, LLP

(57) ABSTRACT

Embodiments of the present invention provide polymer matrix nanocomposites reinforced with nano-scale materials such as nanoparticles and carbon nanotubes and methods of fabricating. The nanomaterials are provided within relatively low weight fractions, for example in the range of approximately 0.01 to about 0.4% by weight and distributed within the matrix by a magnetic mixing procedure to provide substantially uniform reinforcement of the nanocomposites. Advantageously, these nanocomposites provide significantly enhanced tensile strength, strain to failure, and fracture toughness over corresponding neat matrices.

16 Claims, 16 Drawing Sheets

U.S. PATENT DOCUMENTS

| | | | |
|---|---|---|---|
| 2006/0029537 A1 | 2/2006 | Zhang et al. | |
| 2006/0051280 A1 | 3/2006 | Moy et al. | |
| 2006/0054866 A1 | 3/2006 | Ait-Haddou et al. | |
| 2006/0058443 A1 | 3/2006 | Ohashi et al. | |
| 2006/0111501 A1 | 5/2006 | Cont et al. | |
| 2006/0148965 A1 | 7/2006 | Drzal et al. | |
| 2006/0148966 A1 | 7/2006 | Drzal et al. | |
| 2006/0154063 A1 | 7/2006 | Fujihara et al. | |
| 2006/0166003 A1 | 7/2006 | Khabashesku et al. | |
| 2007/0292459 A1* | 12/2007 | Cooper et al. | 424/401 |
| 2008/0110371 A1* | 5/2008 | Hollman et al. | 106/418 |
| 2008/0110372 A1* | 5/2008 | Hollman et al. | 106/418 |
| 2008/0112909 A1* | 5/2008 | Faler et al. | 424/61 |
| 2008/0115694 A1* | 5/2008 | Hollman et al. | 106/418 |

OTHER PUBLICATIONS

International Search Report for PCT/US2006/047483, mailed Aug. 5, 2008.*

International Search Report and Written Opinion for corresponding PCT application PCT/US2006/047483.

Paul Calvert, "A Recipe for strength", *Nature*, 399 (1999) 210-211.

Virginia Yong and H Thomas Hahn, "Processing and Properties of SiC/vinyl ester nanocomposites", *Nanotechnology*, 15 (2004) 1338-1343.

R. P. Singh, M. Zhang and D. Chan, "Toughening of a brittle thermosetting polymer: Effects of reinforcement particle size and volume fraction",*Journal of Materials Science*, 37 (2002) 781-788.

B. Paul, "Prediction of Elastic Constants of Multiphase Materials", *Transactions of the Metallurgical Society of AIME*, 218 (1960) 36-41.

Erik T. Thostenson, Chunyu Li and Tsu-Wei Chou, "Nanocomposites in Context", *Composites Science and Technology*, 65 (2005) 491-516.

* cited by examiner

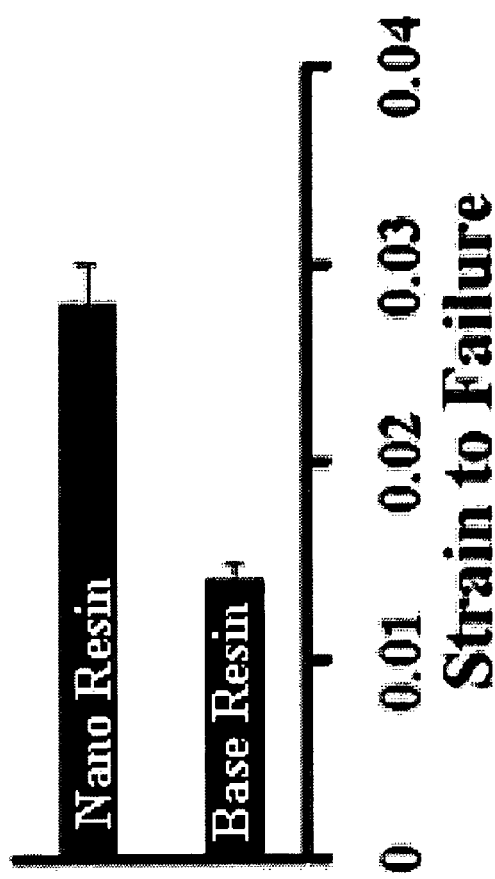
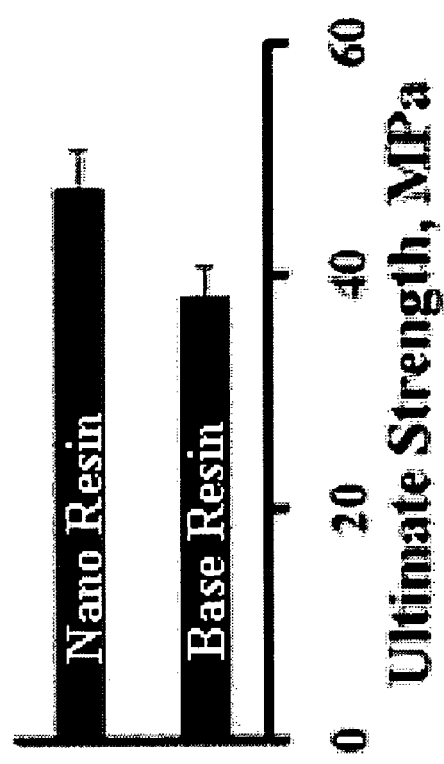
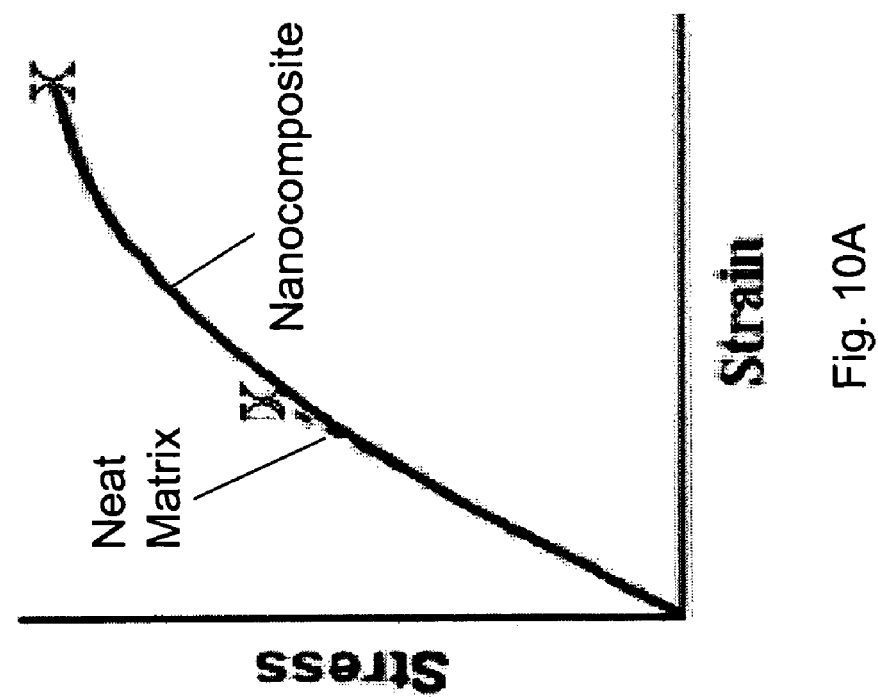
Fig. 10B
Fig. 10C
Fig. 10A

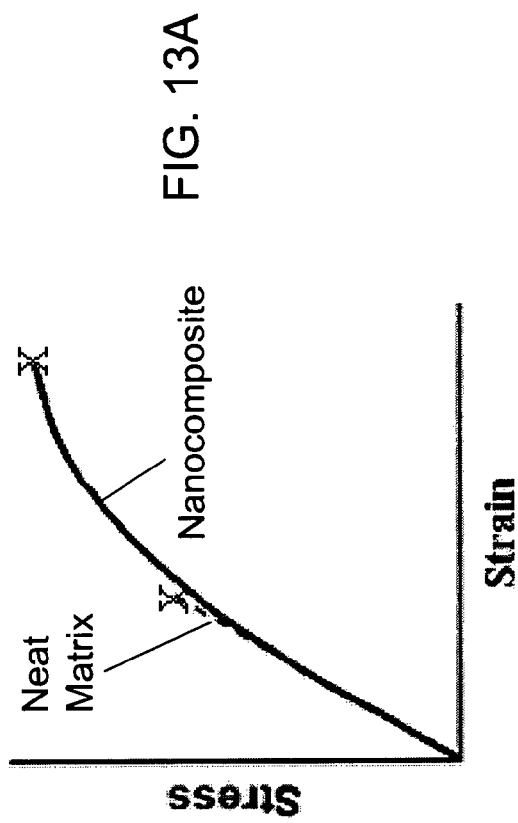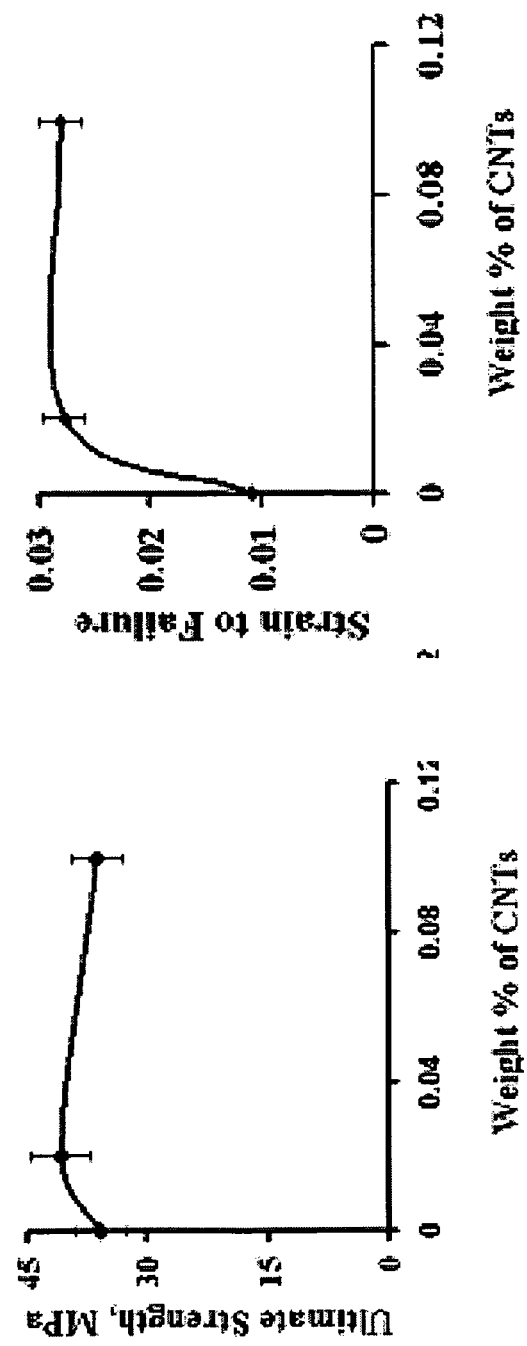
FIG. 13A
FIG. 13B
FIG. 13C

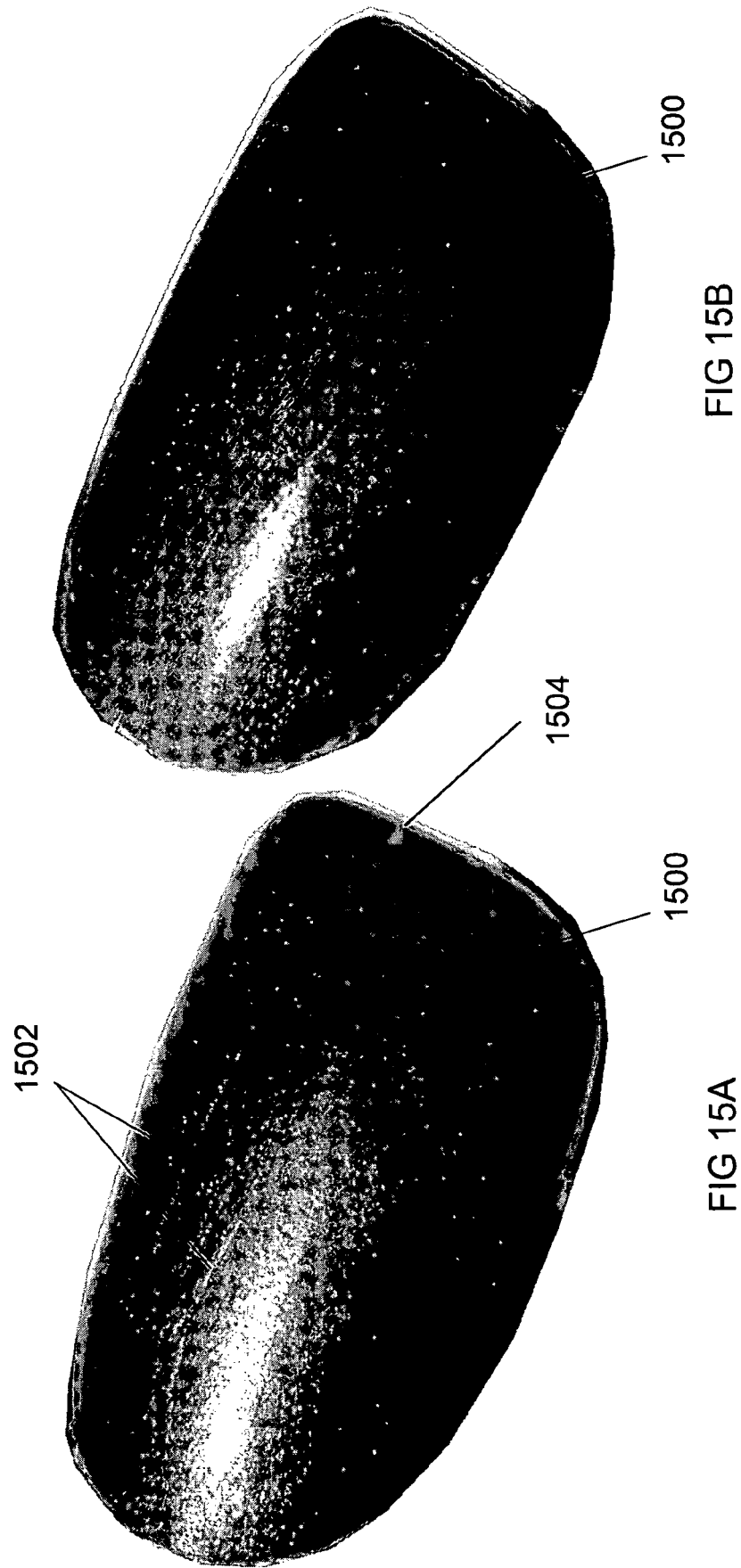

POLYMER MATRIX COMPOSITES WITH NANO-SCALE REINFORCEMENTS

CROSS-REFERENCE TO RELATED APPLICATIONS

This application claims the benefit of priority under 35 U.S.C. § 119(e) to U.S. Provisional Application No. 60/753,006 filed on Dec. 21, 2005, entitled TOUGHENING OF EPOXY USING SIC NANOPARTICLES, U.S. Provisional Application No. 60/753,155 filed on Dec. 20, 2005, entitled TOUGHENING OF POLYESTER RESIN USING TIO2 NANOPARTICLES, and U.S. Provisional Application No. 60/753,496 filed on Dec. 22, 2005 entitled SUPER PERFORMING CNT/EPOXY RESIN, the entirety of each of which is incorporated herein by reference.

STATEMENT REGARDING FEDERALLY SPONSORED R&D

This invention was made with Government support under Contract Number N00014-05-1-05086 awarded by ONR (Office of Naval Research). The Government has certain rights in this invention.

BACKGROUND OF THE INVENTION

1. Field of the Invention

Certain embodiments of the present invention relate generally to composite materials and, in particular, relate to systems and methods for reinforcement of polymer matrices with low concentrations of uniformly dispersed nanomaterials.

2. Description of the Related Art

Composite materials have been developed to meet increasing demands for materials possessing a broad array of desirable properties. Composites are material systems which combine two or more distinct materials, each with its own distinctive, desirable properties, to create a new material with properties that may not be present, or to the same extent, in the components alone. Composite materials, broadly, possess at least two phases—a reinforcement and a matrix. The reinforcement is a material which is embedded within the matrix. In general, the reinforcing material and the matrix material may comprise any combination of metals, ceramics, or polymers.

In one example polymer matrix composites (PMCs) combine strong reinforcing fibers within a polymer matrix. Advantageously, PMCs possess relatively high strength, low weight, and corrosion resistance, which has spurred their development for applications in aerospace, sporting goods, automotive, and other industries where environmental and weight concerns play a key role in design considerations. Furthermore, these materials may be fabricated at relatively low costs, further increasing their desirability.

The use of polymers as matrix materials in composites demands excellent mechanical performance over a large range of temperatures. A limiting factor in the use of polymer matrices, however, is their relative brittleness and tendency to exhibit microcracking at low levels of strain. These microcracks may coalesce under load, forming macrocracks, and due to the relative brittleness of the polymer matrices, result in catastrophic failure with little warning. And while design strains can be kept to low levels to prevent microcracking and catastrophic failure, additional composite material is required to bear the applied load, increasing the total weight of the composite structures.

To mitigate the brittleness and microcracking of polymer matrices, researchers have experimented with the addition of nano-scale materials to polymer matrices in order to improve their strain to failure and fracture toughness. Nano-scale materials possess great promise as composite reinforcements. In general, the greater the surface to volume ratio of a reinforcement, the greater the effectiveness of a material as a reinforcement, and nano-scale materials have a high surface to volume ratio owing to their small size.

Agglomeration, however, has been a significant obstacle to the use of nano-scale materials as reinforcements. Small particles, those having a diameter less than approximately 1 µm, have a strong tendency to agglomerate, or group together, under the influence of Van der Waals forces. In the case of submicron particles, these forces are stronger than gravitational forces and gives rise to spontaneous agglomeration. Agglomerated particles contain small voids which are difficult for the reinforcing matrix to enter by capillary action during processing of the composite. Thus, a reinforced composite formed with agglomerates possesses voids which can act as flaws that, instead of benefiting the composite, are detrimental to its mechanical properties. In particular, a number of studies have observed that the addition of nano-scale materials may improve some mechanical properties, such as fracture toughness or stiffness, while other mechanical properties, such as strength, are detrimentally affected to the point where properties of the composite are less than that of the matrix alone.

Thus, there is need for an improved systems and methods of manufacturing composites reinforced with nano-scale materials and, in particular, polymer matrix composites which have improved fracture properties without incurring substantially detrimental impact upon other mechanical properties.

SUMMARY OF THE INVENTION

One embodiment of the present invention provides a composite material, comprising a matrix material and a reinforcement material. The reinforcement material preferably has at least one dimension of approximately 100 nm or less and is dispersed substantially uniformly within the matrix material. In one embodiment, the reinforcement material is present in a concentration between approximately 0.01% to less than about 1% on the basis of the weight of the composite material. In one embodiment, the matrix is reinforced with nanoparticles in a concentration of between about 0.1% and 0.5% by weight. In a further embodiment, the nanoparticles are provided in the range of approximately 0.2 to less than 0.5 wt %. In another embodiment, the nanoparticles are provided in the range of approximately 0.2 to 0.4 wt %. In an additional embodiment, the nanoparticles are provided in the range of approximately 0.2 to less than 0.4 wt %. In another embodiment, the matrix is reinforced with nanotubes in a concentration of between about 0.01% and 0.1% by weight.

Another embodiment of the present invention provides a SiC-reinforced composite material. The SiC-reinforced composite comprises a matrix material such as epoxy and SiC nanoparticles. The SiC nanoparticles have a diameter of about 100 nm or less and are present in a concentration of between approximately 0.1 to less than about 1%, more preferably less than about 0.9%, and even more preferably between about 0.2 to 0.5% or about 0.2 to 0.4%, on the basis of the weight of the composite material.

In another embodiment, a composite material is provided with titanium dioxide nanoparticle reinforcement. For example, the composite may comprise a polyester resin and about 0.1 wt % to 0.4 wt %, more preferably about 0.2 wt % titanium dioxide nanoparticles.

In another embodiment, a composite material is provided with carbon nanotube reinforcement. For example, the composite may comprise an epoxy resin and a very low weight percentage of carbon nanotubes, e.g., about 0.01% to 0.1% by weight. The nanotubes may have a width or diameter of about 100 nm or less.

In other embodiments, any suitable nano-material loading that causes an increase in ultimate strength of about 10% or more, more preferably about 25% or more, and/or an increase in strain to failure of about 50% or more, may be utilized. In other embodiments, any suitable nano-material loading that causes about a two fold or more rise in $G_{IC}$, and/or about a 20% or more rise in $K_{IC}$, may be utilized.

In another embodiment of the present invention, a method of manufacturing a nanocomposite, such as a polymer nanocomposite, is provided. The method comprises providing a reinforcement material having at least one dimension of approximately 100 nm or less and in a concentration between approximately 0.01 wt % to less than about 1 wt % on the basis of the weight of the composite material. The method further comprises providing a matrix material. The method additionally comprises dispersing the reinforcement material within the matrix material using a magnetic mixing system. A curing agent may be added to the reinforcement-matrix mixture, and the dispersed reinforcement-matrix mixture may be placed within a mold. The method further comprises curing the matrix material.

In a further embodiment, the reinforcement material comprises carbon nanotubes (CNTs), which are first added to a substantially volatile solvent such as ethyl alcohol (EtOH). A sonication technique is then utilized to disperse the CNT's within the solvent. The dispersed solution is then mixed with the resin using the magnetic mixing technique described above. A further sonication technique may be utilized to disperse the CNTs within the resin.

In another embodiment, a nanomaterial-reinforced nail polish is provided. The nail polish may be a composite comprising one or more nail polish coatings and a nanomaterial reinforcement material in one or more of the coatings. In one embodiment, the nanomaterial reinforcement is provided in a concentration of about 0.2 to 0.4 wt % on the basis of the weight of the composite.

These and other objects and advantages of preferred embodiments of the present invention will become apparent from the following description taken in conjunction with the accompanying drawings.

BRIEF DESCRIPTION OF THE DRAWINGS

FIGS. 10A-C present measured tensile properties for embodiments of a $TiO_2$ nanocomposites and the corresponding neat matrix: (10A) Stress-strain response; (10B) Strain to failure as a function of $TiO_2$ loading; (10C) Ultimate tensile strength as a function of $TiO_2$ wt %;

FIGS. 13A-C present measured tensile properties for embodiments of CNT nanocomposites and the corresponding neat matrix: (13A) Stress-strain response; (13B) Strain to failure as a function of CNT loading; (13C) Ultimate tensile strength as a function of CNT wt %;

FIGS. 15A-B present micrographs of artificial nails painted with a single coating of nail polish; (15A) Unreinforced; (15B) Reinforced with $TiO_2$ nanoparticles.

DETAILED DESCRIPTION OF THE PREFERRED EMBODIMENTS

Reference will now be made to the drawings wherein like numerals refer to like parts throughout. Throughout the disclosure, reference to loadings of nano-scale reinforcing materials are provided as wt % on the basis of the total weight of the nanocomposite.

It has been discovered that low weight percentage loadings of nano-scale reinforcing materials, such as nanoparticles and carbon nanotubes, to polymer matrices may be mechanically dispersed during fabrication of polymer nanocomposites to provide nanocomposites which are substantially free of agglomerates. As described herein, nano-scale reinforcing materials according to certain embodiments have at least one dimension of about 100 nm or less. More preferably, the nano-scale reinforcing materials have two dimensions of about 100 nm or less. It will be appreciated, however, that other embodiments of the invention may not be limited to these particular dimensions.

In one non-limiting embodiment, the nano-scale reinforcement may comprise nanoparticles having a diameter of approximately 100 nm or less. Such nanoparticles may be elemental, oxide or non-oxide ceramics, metallic alloys and intermetallics, or combinations thereof. More preferably, certain embodiments described herein are directed to ceramic or elemental nanoparticle reinforcements. In a further non-limiting embodiment, the nano-scale reinforcement may comprise carbon nanotubes having a diameter of approximately less than 100 nm. Advantageously, polymer nanocomposites so fabricated possess significantly enhanced fracture toughness while concurrently preserving or improving their tensile properties, such as tensile strength, elastic modulus, and strain to failure, over comparable un-reinforced polymers.

Figure 1B:
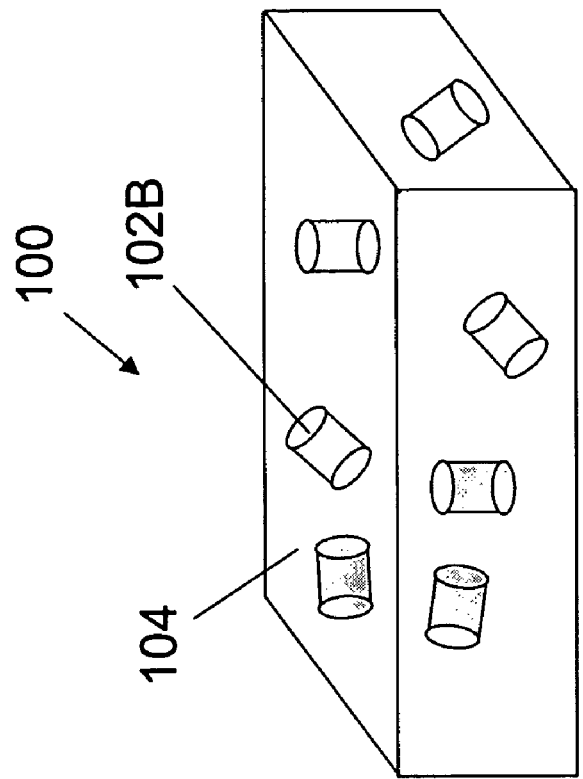
FIGS. 1A-B are schematic illustrations of embodiments of nanocomposites having substantially uniformly distributed nanomaterials: (1A) Nanoparticles; (1B) Carbon Nanotubes.
Figure 1A:
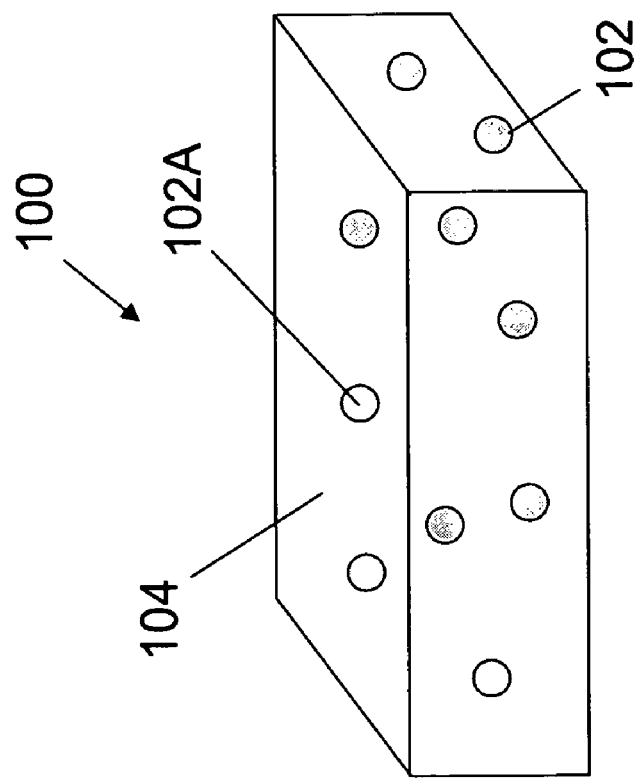

FIGS. 1A-B present embodiments of a nanocomposite 100 having substantially uniformly distributed nano-scale reinforcements 102 possessing substantially low levels of agglomerates, designed for improved fracture toughness and strain to failure. In certain embodiments, the nanocomposite 100 comprises a polymer matrix 104 reinforced with nanoparticles 102A (FIG. 1A) or carbon nanotubes 102B (FIG. 1B), which are substantially uniformly distributed within the matrix 104 during processing. In one embodiment, the weight fraction of the nano-scale reinforcement 102, or loading, is relatively low, on the order of approximately 0.02% to 1.5%. In a preferred embodiment, the loading is in the range of approximately 0.02% to less than approximately 1 wt %. Higher loadings may be used, as necessary, depending on factors such as the nano-scale reinforcement 102 and the ability to disperse the reinforcement within the matrix 104. In further embodiments, nano-reinforcement 102 is substantially dispersed using a magnetic mixing process, as discussed below. So fabricated, i.e., using low loading percentages and mixing as disclosed above here and with proper mixing technique as employed here, embodiments of the nanocomposites 100 possess less substantially no agglomerated nano-scale reinforcements 102 (as shown in FIGS. 2C-E below), where the agglomerates comprise a plurality of individual nano-scale reinforcements 102 in contact with one another, on the basis of the total amount of reinforcing material 102 added. Advantageously, nanocomposites 100 within these loading ranges may concurrently demonstrate significantly improved tensile strength, strain to failure, and fracture toughness over comparable, un-reinforced neat matrices, as discussed in detail below.

In a non-limiting embodiment, the matrix 104 may comprise a polymer. In a preferred embodiment, the polymer may comprise a high temperature epoxy based on diglycidyl ether of bisphenol A (DGEBPA) and alkylglycidyl ether (AE), or DGEBPA-AE. In an alternative embodiment, the polymer matrix may comprise a polyester. In further alternative embodiments, the matrix may comprise other polymers or polymer precursors such as pre-ceramic polymers. One preferred embodiment of a pre-ceramic polymer comprises KiON CERASET®.

In non-limiting embodiments, the nano-scale reinforcements 102 may comprise nanoparticles 102A of elements, oxide and non-oxide ceramics, metallic alloys and intermetallics, or combinations thereof. In preferred embodiments, the nanoparticles 102A may comprise Titanium Dioxide ($TiO_2$), Yttrium Oxide ($Y_2O_3$), Zinc Oxide (ZnO), Silicon Carbide (SiC), and Carbon (C) or combinations thereof. In one particularly preferred embodiment, a single nanoparticle species is utilized as a reinforcement. The nanoparticles 102A may further range in size from approximately 15 nm to 45 nm and are provided in a relatively low weight fraction with respect to the total weight of the nanocomposite. In one embodiment, the nanoparticles 102A are provided in the range of approximately 0.2 to 1.5 wt %, more preferably less than about 1 wt %. In an alternative embodiment, the nanoparticles 102A are provided in the range of approximately 0.2 to 0.5 wt %. In a further embodiment, the nanoparticles 102A are provided in the range of approximately 0.2 to less than 0.5 wt %. In another embodiment, the nanoparticles 102A are provided in the range of approximately 0.2 to 0.4 wt %. In an additional embodiment, the nanoparticles 102A are provided in the range of approximately 0.2 to less than 0.4 wt %.

In a further non-limiting embodiment, the nano-scale reinforcement 102 may comprise carbon nanotubes 102B. Carbon nanotubes 102B are a relatively new configuration of carbon which exhibit a variety of superior mechanical properties. Progress made in the production and purification of nanotubes in recent years has made it practical to consider nanotubes 102B as reinforcements in composite materials. With respect to their mechanical properties, nanotubes 102B exhibit extraordinary strength, on the order of tens of GPa, and elastic moduli on the order of about 1 TPa. Additionally, nanotubes 102B may undergo plastic deformation at elevated tensile stresses, allowing for some degree of permanent deformation. This deformation begins at strains of approximately 5% and can increase the maximum strain the tube undergoes before fracture. These mechanical properties make CNTs 102B excellent candidates as reinforcing materials. Further, carbon nanotubes 102B possess a relatively low density for a solid, approximately 1.3-1.4 $g/cm^3$. This provides CNTs 102B a specific strength which is very high, also making them very attractive for use in composite materials, which are often utilized in applications where weight is a key design consideration.

In one embodiment, the CNTs 102B may comprise single walled carbon nanotubes (SWNTs) and/or multiple walled carbon nanotubes, MWNTs. SWNTs can be conceptualized as wrapping a one-atom-thick layer of graphite called graphene into a seamless cylinder, while MWNTs are multiple layers of graphite rolled upon themselves to form a tube shape. CNTs 102B possess diameters on the order of about 1 nm with tube lengths that can be many thousands of times larger. In one preferred embodiment, the CNTs 102B comprise SWNTs having lengths in the range of approximately 1 to 500 micrometers. In further embodiments, the SWNTs are provided at loadings of approximately 0.02 to 0.1 wt %.

As discussed in greater detail with respect to the examples below, the use of substantially uniformly dispersed nanoparticles or CNTs 102B as reinforcements for nanocomposites 100 provides improved fracture toughness while concurrently preserving or improving the tensile properties of the nanocomposite 100, such as tensile strength and strain to failure, compared to un-reinforced neat matrices. In one embodiment, the carbon nanotubes 102B are provided in the range of approximately 0.01 to 0.1 wt %. In further alternative embodiments, the loading fraction of the nano-scale materials may be adjusted within this range as generally understood by one of skill in the art so as to provide nanocomposites 100 having combinations of mechanical properties which are elevated above those of the un-reinforced matrix.

Figures 2A, 2B:
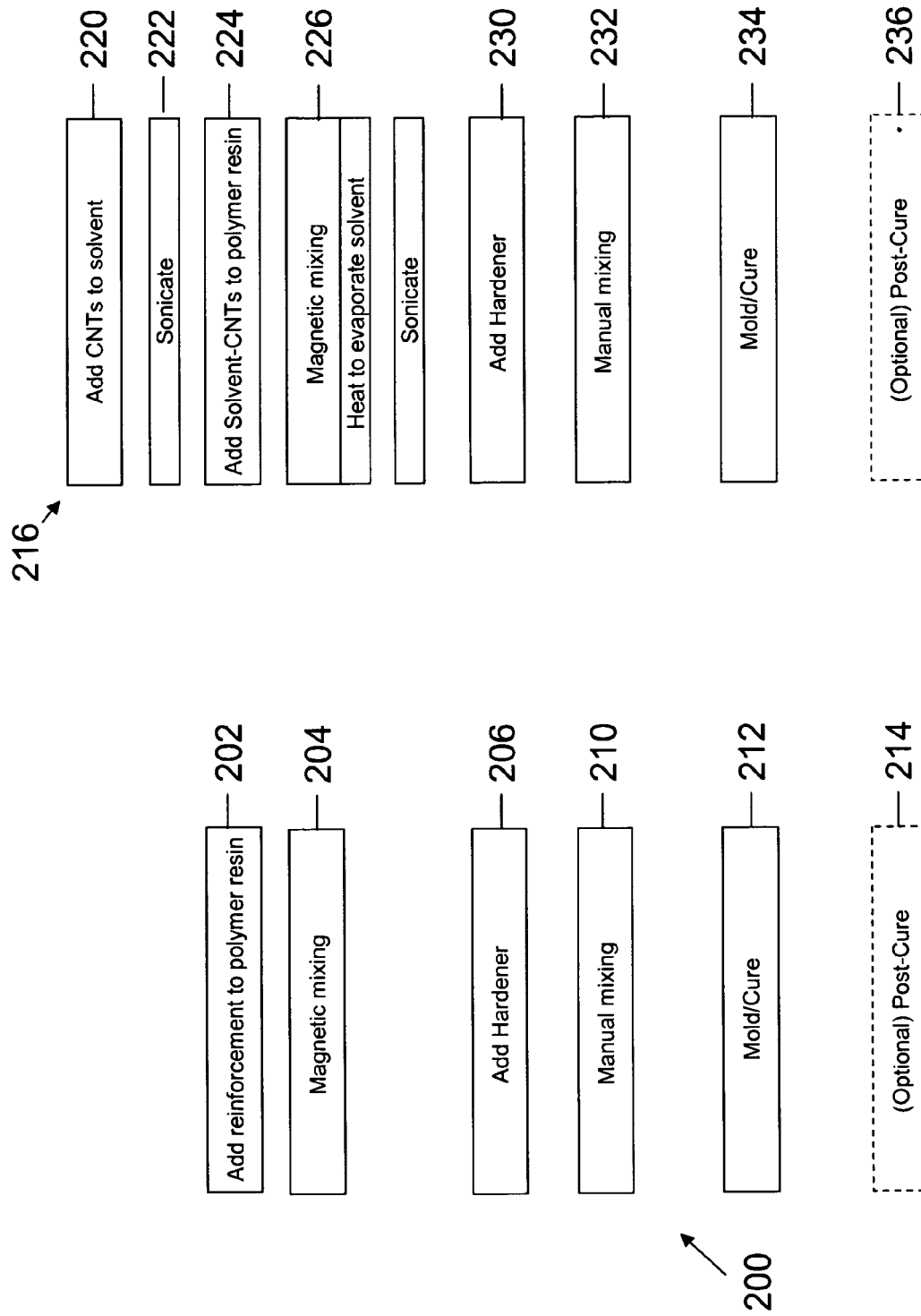
FIGS. 2A and 2B are embodiments of methods for manufacture of the nanocomposites having substantially uniformly distributed nanoparticles (FIG. 2A) and carbon nanotubes (FIG. 2B)
Figure 2E:
FIGS. 2C-E illustrate embodiments of nanocomposites containing a SiC nanoparticle reinforcement at loadings of 0.2% (2C), 1% (2D), and 1.5% (2E)
Figure 2D:
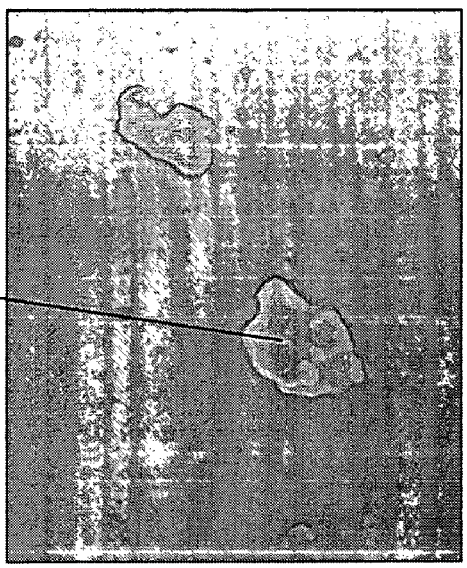
Figure 2C:
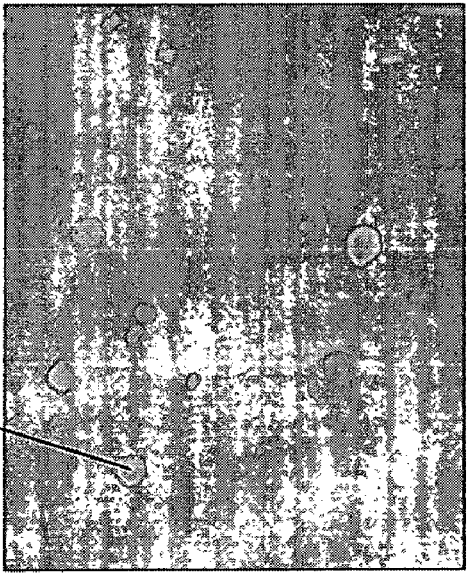

One embodiment of a method 200 by which nanocomposites having substantially uniformly distributed nanoparticles may be fabricated is illustrated in FIG. 2A. In a first step 202, a predetermined, low weight loading of nanoparticles is added to a matrix material which is contained within a beaker or other vessel. The nanoparticle material, size, and loading fraction may be varied, as discussed above. In a non-limiting example of the method, the matrix material will be referred to as a polymer resin, however, as discussed above, the matrix is not limited to polymer materials.

In a second step 204, the nanoparticle-resin mixture is mechanically mixed using a magnetic mixing system. In one embodiment, the magnetic mixing system comprises a magnetic stirring device and a magnetic stirring bar. The magnetic stirring bar is added to the beaker and the beaker is placed upon the magnetic stirring device. Activation of the stirring device causes the stirring bar to rotate using non-contact magnetic torque, providing mechanical mixing of the nanoparticle-matrix mixture. The magnetic mixer is operated according to a predetermined schedule of mixing time and rpm, based on the matrix and nanoparticle materials. In one embodiment, approximate values for magnetic mixing times and speeds which may provide a substantially uniform distribution of nanoparticles within the matrix are provided as illustrated below in Table I and discussed in greater detail below with respect to the examples.

TABLE I

Nanoparticle mixing schedule

| Nanoparticle | Matrix | Magnetic Mixing RPM | Magnetic Mixing Time (h) | Manual Mixing Time (min) | Cure Time (h) | Post-Cure Temp (°C.) | Post-Cure Time (h) |
|---|---|---|---|---|---|---|---|
| SiC | DGEBPA-AE | 1200 | 10 | 20-30 | 3 | 120 | 1 |
| TiO$_2$ | Polyester | 1500 | 700 | 5 | 4 | N/A | N/A |

In alternative embodiments, the magnetic mixing speed and time may be increased or decreased as necessary In a third step 206, a curing agent such as a hardener is added to the resin-nanoparticle mixture. In one embodiment, the resin to hardener ratio is provided in accordance with the manufacturer's instruction. In a non-limiting example, a resin to hardener ratio of approximately 3:1 may be used with DGEBPA-AE epoxy, while a ratio of approximately 30 mL to 10 drops may be used with polyester resins. In alternative embodiments, the ratio of hardener to resin may be increased or decreased as necessary to cure the nanocomposite.

In a fourth step 210 of the method 200, the nanoparticle-resin mixture is subjected to a manual mixing procedure for a predetermined time. The mixture is stirred with a stirring rod or other device or implement generally known in the art for hand mixing. The mixing is performed at a linear speed of approximately 1 cm/sec to avoid foaming of the mixture. In one embodiment, the manual mixing is conducted over the time range of approximately 5 to 30 minutes, as illustrated in Table I above. In alternative embodiments, the manual mixing time and linear speed may be increased or decreased.

In a fifth step 212, following mixing, the nanoparticle-resin mixture is poured into a polished aluminum mold or other mold and allowed to cure in air. Cure times and temperatures are, in one embodiment, provided in accordance with the resin manufacturer's instructions. In one embodiment, the nanocomposite is cured at approximately room temperature for times ranging between approximately 3 hours to 4 hours. In alternative embodiments, the cure time and temperature may be increased or decreased.

In alternative embodiments, the cured nanocomposite may be subjected to a sixth step 214 comprising a post-cure at elevated temperature. In one embodiment, the post-cure schedule comprises heat treatment at approximately 120° C. for approximately one hour.

In one embodiment, a method 216 of manufacture of CNT reinforced nanocomposites (FIG. 2A) builds upon the framework of the first method 200 described above (FIG. 2A), using additional steps. The second method 216 utilizes these additional steps in order to disperse the CNTs, as a high degree of adhesion is present between CNTs which can make SWNTs difficult to separate into single units from aggregates and clusters within the viscous polymer matrix during processing.

In a first step 220 of the second method 216, a predetermined, low weight loading of nanotubes is added to a substantially volatile solvent which is contained within a beaker or other vessel. In one embodiment, ethyl alcohol (EtOH) is a used as the volatile solvent, owing to its relatively high volatility and its low viscosity compared to the polymer resin. However, in alternative embodiments, other volatile solvents may be used, such as, in non-limiting embodiments, other alcohols and acetone. The size, and loading fraction of the nanotubes, may be varied, as discussed above.

In a second step of the method 222, the beaker is subsequently placed in a sonication water bath which utilizes sound waves to cause vibrations within the water which are transferred to the CNT-EtOH solution. In one embodiment, sonication is performed for approximately five hours at room temperature to generate a substantially uniform distribution of CNTs within the EtOH.

Subsequently, in a third step 224 of the method 216, the dispersed EtOH-CNT solution is mixed with the resin using the magnetic mixing technique discussed above. In one embodiment, the resin comprises DGEBPA-AE. In a further embodiment, the magnetic stirring bar rotates at approximately 700 RPM at approximately room temperature for approximately 15 hours At the end of the mixing period, further stirring is performed at approximately the same speed at about 80° C. for approximately 45 minutes. In this manner, the volatile EtOH or other CNT dispersion solvent is substantially removed from the resin-CNT mixture.

In a fourth step 226 of the second method 216, sonication is performed a second time as in order to ensure substantially uniform dispersion of the CNTs within the resin prior to curing. In one embodiment, the resin-CNT mixture is sonicated for approximately 25 minutes.

In a fifth step 230 of the second method 216, the hardener is added to the resin-CNT mixture. In a non-limiting example, a resin to hardener ratio of approximately 3:1 is used with DGEBPA-AE epoxy. In alternative embodiments, the ratio of hardener to resin may be increased or decreased.

In a sixth step 232 of the second method 216, the mixture is subjected to a manual mixing procedure for a predetermined time. The mixture is stirred with a stirring rod or other device generally known in the art for mixing by hand. The mixing is performed at a linear speed of approximately 1 cm/sec to avoid foaming of the mixture. In one embodiment, the manual mixing is conducted for approximately 20-30 minutes. In alternative embodiments, the manual mixing time and linear speed may be increased or decreased, as necessary to ensure substantially uniform distribution of the CNTs within the resin.

In a seventh step 234, following mixing, the mixture is poured into a polished aluminum mold or other mold and allowed to cure in air. Cure times and temperatures are, in one embodiment, provided in accordance with the polymer manufacturer's instructions. In one embodiment, the nanocomposite is cured at approximately room temperature for approximately 5 hours. In alternative embodiments, the cure time and temperature may be increased or decreased.

In an eighth step 236 of the method 216, the nanocomposite may be optionally subjected to a post-cure treatment. In one embodiment, the post-cure comprises heat treatment at approximately 120° C. for approximately one hour.

Nanocomposites fabricated according to the methods 200, 216 may possess substantially low levels of agglomerates. FIG. 2C-E present embodiments of SiC-reinforced nanocomposites at loading fractions of 0.2, 1, and 1.5 wt %, respectively. It is observed that at 0.2 wt %, the nano-scale reinforcements 102 are substantially uniformly distributed and unagglomerated 240. In contrast, at loadings of 1 and 1.5 wt %, relatively large agglomerates 242 of the nano-scale materials are observed, with the size of the agglomerates 242 increasing with increasing loading.

EXAMPLES

Bulk Nanocomposites

In the following examples, testing is performed on nanocomposites reinforced using nanoparticles and carbon nanotubes and their corresponding neat matrices in order to illustrate the property improvements which may be achieved in these composites over comparable un-reinforced polymer materials. In particular, the tensile and fracture properties are examined. The nanocomposites tested are formed as described above, using two commonly available nanoparticles, SiC and $TiO_2$, and SWNTs with matrices of DGEBPA-AE and polyester. Advantageously, these polymers are representative of those commonly used in present composites manufacturing, room temperature cure polymers and high temperature cure epoxies, and thus provide results which are relevant to present applications. To assess the influence of the nano-scale reinforcements on the performance of the nanocomposites, neat matrices were formed without the reinforcements.

Bulk Nanocomposites: Mechanical Testing

In the examples, mechanical characterization focuses on evaluation of the tensile and fracture properties of embodiments of the nanocomposite and corresponding neat matrix. Tensile properties of the neat matrices and nanocomposites are measured according to ASTM D638, Standard Test Method for Tensile Properties of Plastics. Dogboned uniaxial tensile specimens 300 of each material are provided having dimensions consistent with the standard (FIG. 3A). Tests are conducted using an Instron™ type 4200 universal testing machine and the load (P) and displacement (d) are recorded. Strain along the loading axis of the composite is also measured and recorded using strain gauges 302 bonded to the specimen 300. From the stress-strain data, the elastic modulus, yield stress, ultimate stress, and strain to failure are determined in accordance with the standard. For each material condition, at least four specimens were tested.

The fracture properties of the nanocomposites and neat matrices are quantified by measurement of the critical stress intensity factor, $K_{IC}$, and the critical strain energy release rate, $G_{IC}$, through single edge notch bend tests (SENB) performed according to ASTM D5045, "Standard Test Method for Plane-Strain Fracture Toughness and Strain Energy Release Rate of Plastic Materials." $K_{IC}$ and $G_{IC}$ are material properties which provide a measure of the resistance of a material to crack propagation in the presence of a sharp crack in a Mode I, or tensile mode. $K_{IC}$ scales with the load at which crack propagation begins, while $G_{IC}$ scales with the fracture work.

Figure 3B:
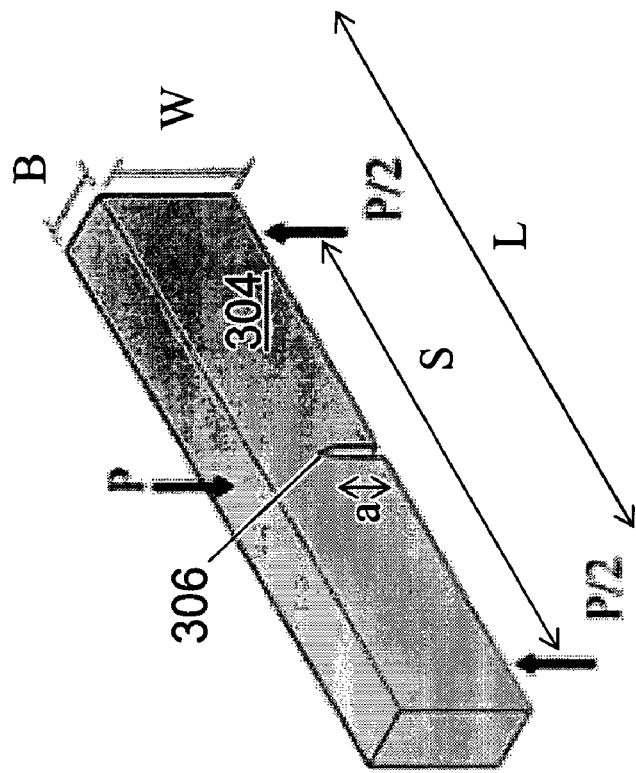
FIGS. 3A-3B are schematic illustrations of test specimens for measurement of tensile and fracture properties of the nanocomposites of FIGS. 1A-B.
Figure 3A:
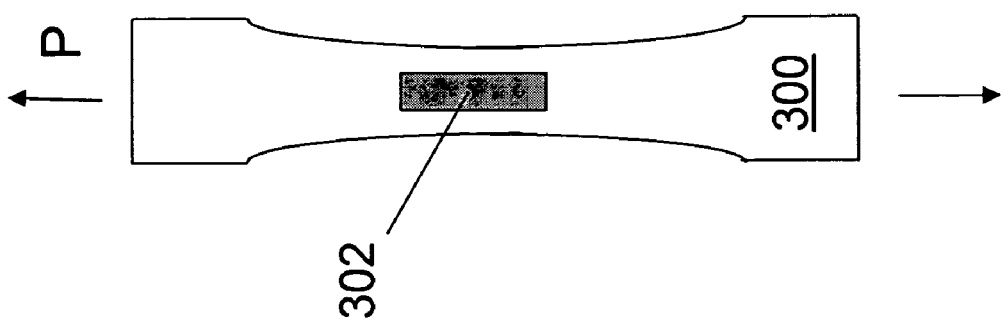

The SENB test specimen 304 is illustrated in FIG. 3B. The SENB specimen 304 comprises a generally rectangular beam having a length L, a width, W, a thickness B. A notch 306 of length, a, is introduced into the SENB specimen 304, approximately centered on the length, extending in the width direction. The SENB specimen 304 is loaded in flexure at a rate of approximately 0.25 mm/min, approximately opposite the notch 306, and supported at positions flanking the notch 306, separated by a span length S, and centered approximately on the notch 306. So configured, the SENB specimen 304 is loaded in compression, with monotonically increasing load, P, causing the specimen 304 to bend downwards. Load and displacement of the specimen 304 at the load line are measured and the notch 306 is monitored to identify the load at which crack propagation initiates at the notch 306.

$K_{IC}$ is calculated according to the standard ASTM D5045. The validity of the plain strain $K_{IC}$ value so calculated is verified using Equation (1):

$$B, a, \text{ and } (W - a) > 2.5\left(\frac{K_{IC}}{\sigma_y}\right)^2 \qquad (1)$$

where $\sigma_y$ is the yield stress, calculated from a 0.2% offset applied to the tensile stress-strain curve.

$G_{IC}$ is calculated using the load-displacement response of the SENB specimen 306 according to ASTM D5045. A corrected displacement is obtained from an indentation test outlined in the standard. $G_{IC}$ is then determined from the energy given by the area under the load-displacement curve using Equation (2):

$$G_{IC} = \frac{U}{BW\varphi} \qquad (2)$$

where U is the corrected energy and $\varphi$ is an energy calibration factor.

In some cases, fracture surfaces of the SENB specimens 306 are also examined using a Hitachi S-4800 Field Emission Scanning Electron Microscope (SEM). Fracture surfaces are covered with a thin layer of sputtered gold and imaged in the SEM using an acceleration voltage of approximately 1 kV.

Bulk Nanocomposites: SiC Nanoparticle Reinforced Nanocomposites

Investigations below illustrate the effect of inclusion of low loadings of SiC nanoparticles on the tensile and fracture properties of embodiments of the nanocomposites and comparable un-reinforced neat matrices. An epoxy based on DGEBPA-AE is mixed with SiC nanoparticles (Accumet Materials Co.). The SiC nanoparticles possess a density of about 3.22 g/cm$^3$, a surface area of 70-90 m$^2$/g, and a size n ranging between about 45 to 55 nm. Four weight fractions of SiC nanoparticles are investigated: 0.2, 0.5, 1, and 1.5%. The SiC nanoparticles are added to the epoxy resin and the mixture is stirred using the magnetic mixing device for approximately 10 hours at about 1200 rpm in order to disperse the nanoparticles within the matrix resin. Subsequently, the hardener is added to the homogeneous mixture in an epoxy to hardener ratio of approximately 3:1. Following addition of the hardener, the mixture is stirred manually for approximately 20-30 minutes at a rate of approximately 1 cm/sec. Following mixing, the mixture is poured into a polished aluminum mold and allowed to cure in air at room temperature for approximately 3 hours. Subsequently, the cured composites are post-cured for approximately 1 hr at about 120° C. in air. To quantify the effect of low SiC nanoparticle loading on the performance of the composite, an epoxy panel without SiC nanoparticles is also manufactured using the same procedure.

Figure 4A:
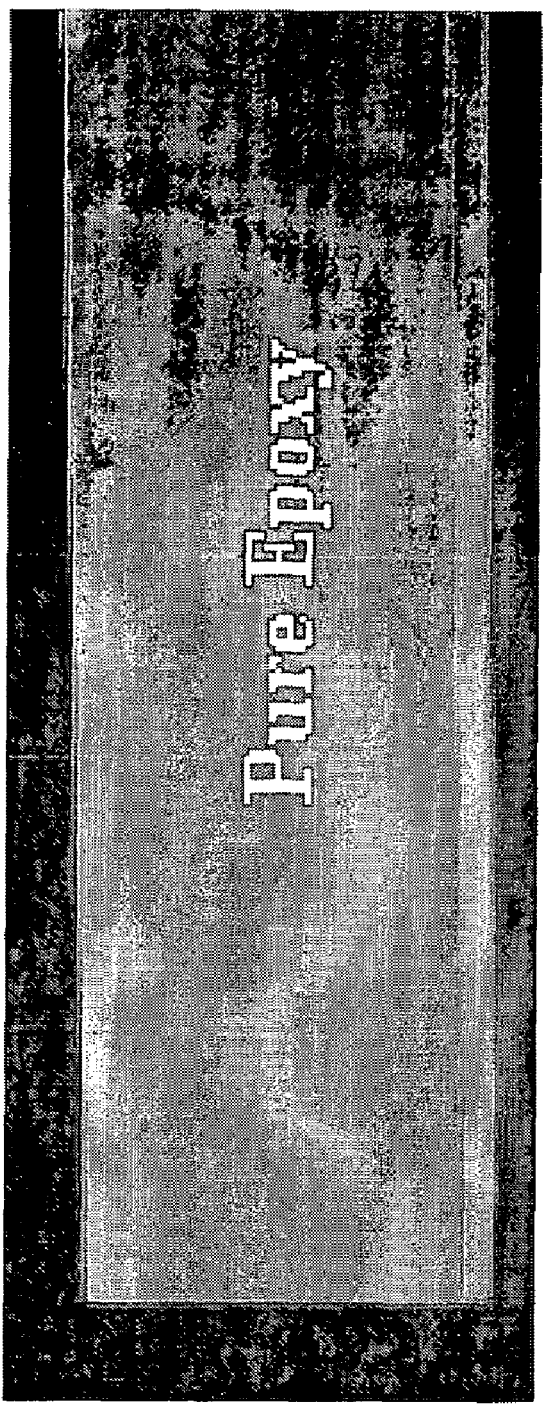
FIGS. 4A-B are micrographs of as-processed neat matrix and SiC reinforced nanocomposites.
Figure 4B:
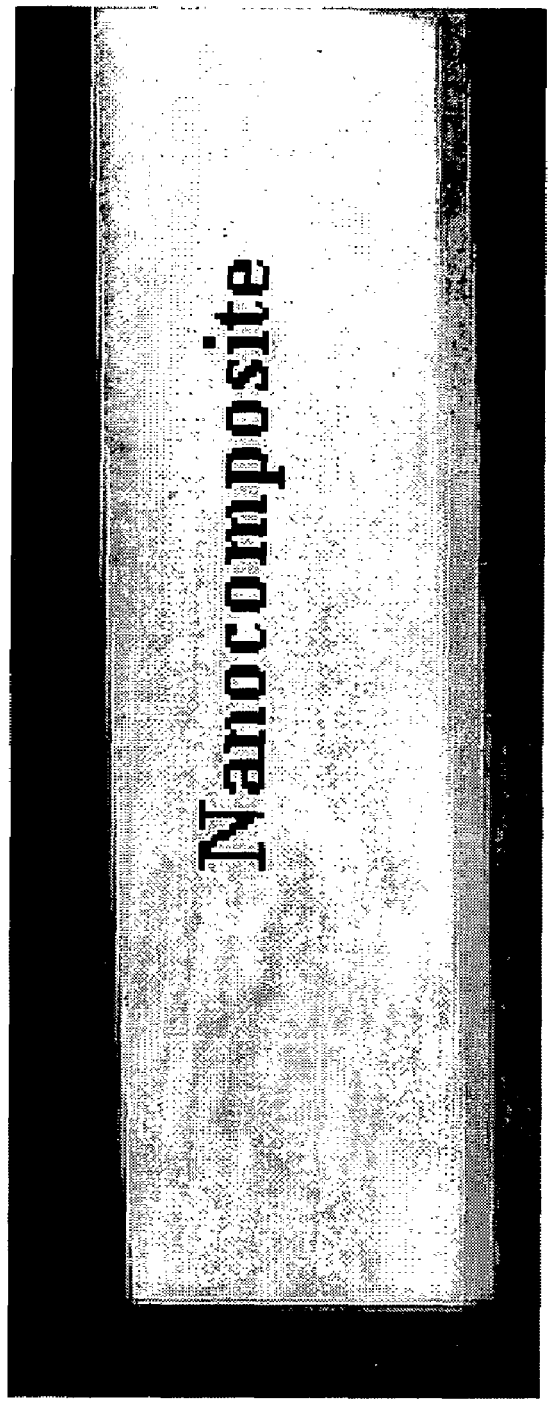
Figure 5E:
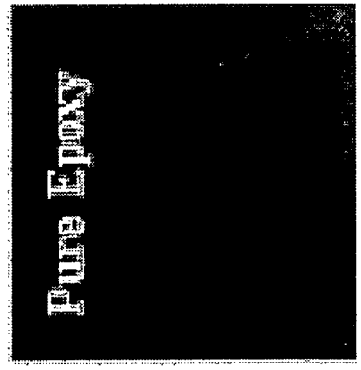
FIGS. 5A-E are micrographs of embodiments of an as-processed neat matrix and SiC nanocomposites at loadings of approximately 0.2, 0.5, 1, and 1.5%, respectively.
Figure 5D:
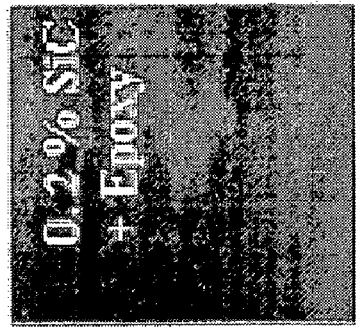
Figure 5C:
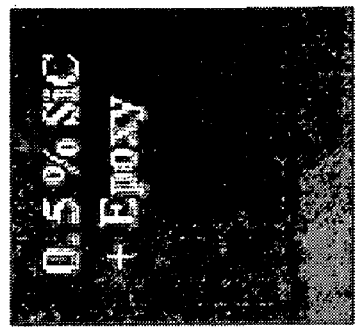
Figure 5B:
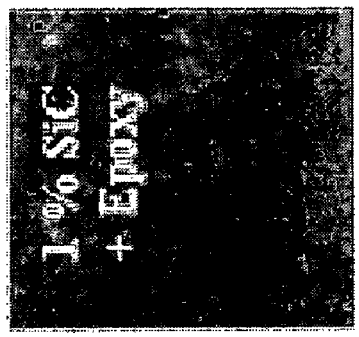
Figure 5A:
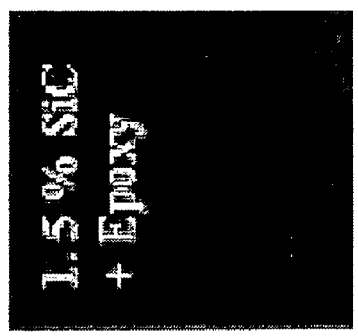

FIGS. 4A-B illustrates the appearance of the as-processed neat matrix and SiC-reinforced nanocomposite of approximately 0.2% to 0.4% SiC by weight. It is apparent from the micrographs of FIG. 4A-B, the SiC reinforced nanocomposites (4B) present an ash-colored appearance, while the neat matrix (4A) is approximately transparent. In one aspect, this result demonstrates that even small loadings of nanoparticles are sufficient to change the optical properties of the nanocomposite from those of the neat matrix from transparent to opaque. In another aspect, this result indicates that the mixing procedure described above provides substantially homogeneous dispersion of the nanoparticles within the resin, as the appearance of the nanocomposite is approximately uniform.

The appearance of an as-processed neat matrix and SiC nanocomposites at loadings of approximately 0.2, 0.5, 1, and 1.5% are provided in FIGS. 5A-E. Examining the appearance of the nanocomposites, it is apparent that poorer dispersion of the SiC nanoparticles takes place at the higher loading fractions of 1 and 1.5% (FIGS. 5D and 5E), even though each material condition has undergone the same processing method and nanoparticle distribution procedure. Examining the micrographs of FIGS. 5A-E in order of increasing loading fraction, from left to right, the appearance of the 0.2 and 0.5 wt % nanocomposites (FIGS. 5B and 5C) appear approximately uniform, indicating homogeneous dispersion of the SiC nanoparticles. Even better uniformity is found in the 0.2 wt % sample, indicating that loadings of less than 0.5 wt % may be particularly advantageous. With loadings of 1 and 1.5% SiC, however, the nanocomposites exhibit dark and light areas, indicating that agglomeration occurs in these higher loading nanocomposites. This inhomogenaeity may negatively affect the composite properties, as illustrated below.

Dogboned tensile specimens were employed for measurement of the tensile properties of the two materials using ASTM D638. At least four specimens were tested for each material condition. FIGS. 6A-D below present the tensile properties of embodiments of the SiC-DGEBPA-AE nanocomposites and corresponding neat matrix.

Figure 6A:
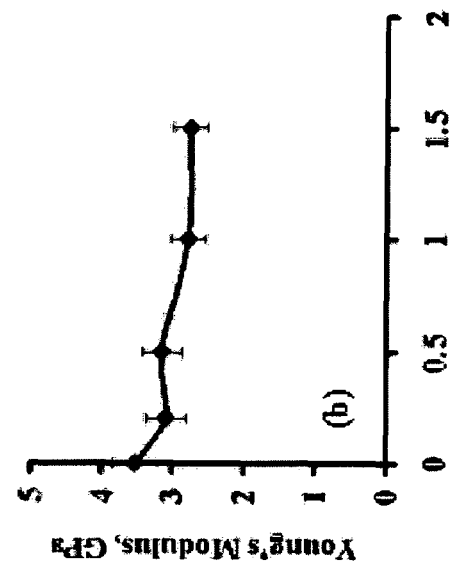
FIGS. 6A-D present measured the tensile properties for embodiments of SiC nanocomposites and the corresponding neat matrix: (6A) Tensile stress-strain response; (6B) Young's Modulus as a function of SiC loading; (6C) Ultimate tensile strength as a function of SiC loading; (6D) Strain to failure as a function of SiC wt %.

Examining representative stress-strain curves for the nanocomposite with weight fraction of approximately 0.2% to 1.5% SiC as well as the neat matrix, FIG. 6A, the un-reinforced neat matrix is observed to fail in a brittle manner, with the stress-strain curve rising linearly to failure. In contrast, nanocomposites containing 0.2-0.4% SiC nanoparticles exhibit yielding prior to failure, as illustrated by the non-linear portion of the curves at elevated values of stress. Nanocomposites containing 1% and 1.5% exhibit brittle failure, similar to the neat matrix.

Figure 6B:
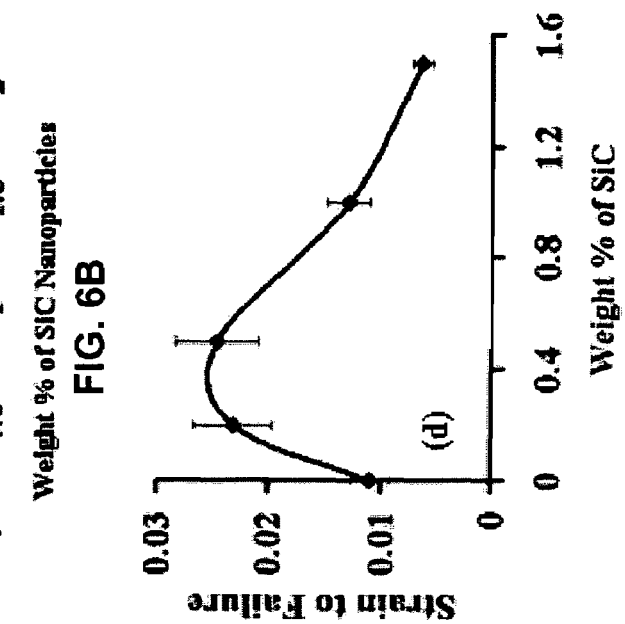
Figure 6C:
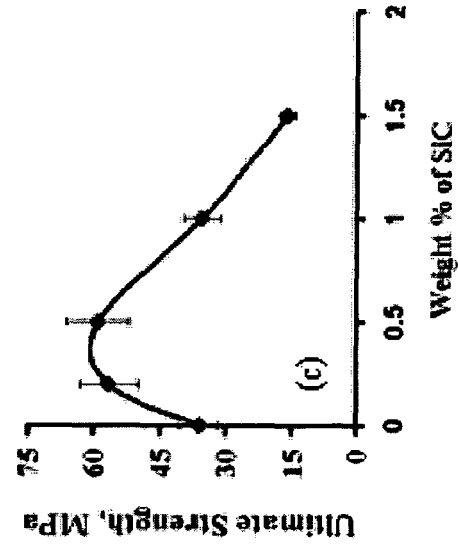
Figure 6D:
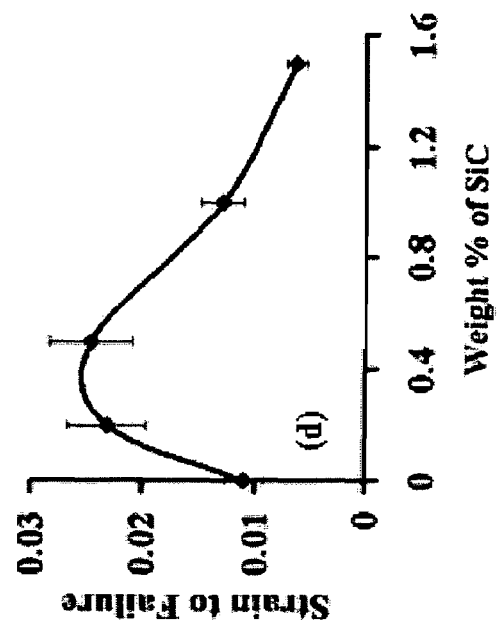

FIGS. 6B-D compare the ultimate strength, strain to failure, and elastic modulus of the SiC reinforced nanocomposite compared to the baseline neat matrix, illustrating that the ultimate strength and strain to failure of the nanocomposites increase significantly with low nanoparticle loadings. In the range of nanoparticle loadings from 0.2-0.5%, the ultimate strength rises from about 35 MPa in the neat matrix to about 57-60 MPa in the range of 0.2-0.5% loadings, an increase of more than about 70% over the un-reinforced matrix. Thus, generally for a loading of about 0.4 wt %, the ultimate strength may increase by about 70% or more compared to the un-reinforced matrix. In other embodiments, any suitable nanoparticle loading that causes an increase in ultimate strength of about 10% or more, more preferably about 25% or more, and even more preferably about 50% or more, may be utilized. The strain to failure is also found to benefit over this range of nanoparticle loadings, increasing to about 0.024 at 0.5% loading from about 0.011 in the neat matrix, an increase of more than 200% over the un-reinforced matrix, an increase of over 150%. In other embodiments, any suitable nanoparticle loading that causes an increase in strain to failure of about 50% or more may be utilized.

Beyond approximately 0.5% loadings, both strength and failure strain are found to diminish with increased SiC loading, falling below the values of the neat matrix at a loading of 1.5%. In fact, the predicted curves shown in FIGS. 6C and 6D indicate that even at about 0.5% loading, strength and strain to failure may begin to decrease; thus, loadings less than about 0.5% wt %, e.g., up to about 0.4 wt %, may be advantageous. For example, at about 1% SiC loading FIGS. 6C and 6D show approximately no change in strength and strain to failure, and at about 1.5% SiC loading there is about a −55% and −50% drop in strength and strain-to-failure, respectively, compared to the neat matrix. Further, over the range of SiC loadings investigated, the elastic modulus remains approximately constant with the increase in nanoparticles, decreasing only slightly, approximately 14%, when initially added to the polymer matrix. Thus, low loadings of SiC nanoparticles, for example between about 0.2-0.5%, and even between about 0.2 and 0.4%, significantly improve the tensile properties of polymer nanocomposites.

An exemplifying SENB fracture specimen 304 is illustrated in FIG. 3B. In one embodiment, the fracture specimen 304 has a nominal width of about 25.4 mm, a span length of about 112 mm, and an average thickness of approximately 6.4 mm. A notch 306 of approximately 12 mm in length and 1.5 mm in width is cut using a milling cutter and sharpened using a razor blade tapped into the notch. The SENB specimens 304 so provided have a nominal crack length to specimen width ratio a/W, of approximately 0.5, satisfying the ASTM standard's requirement for a valid SENB test. At least four such specimens were tested for each material condition.

Figures 7A, 7B:
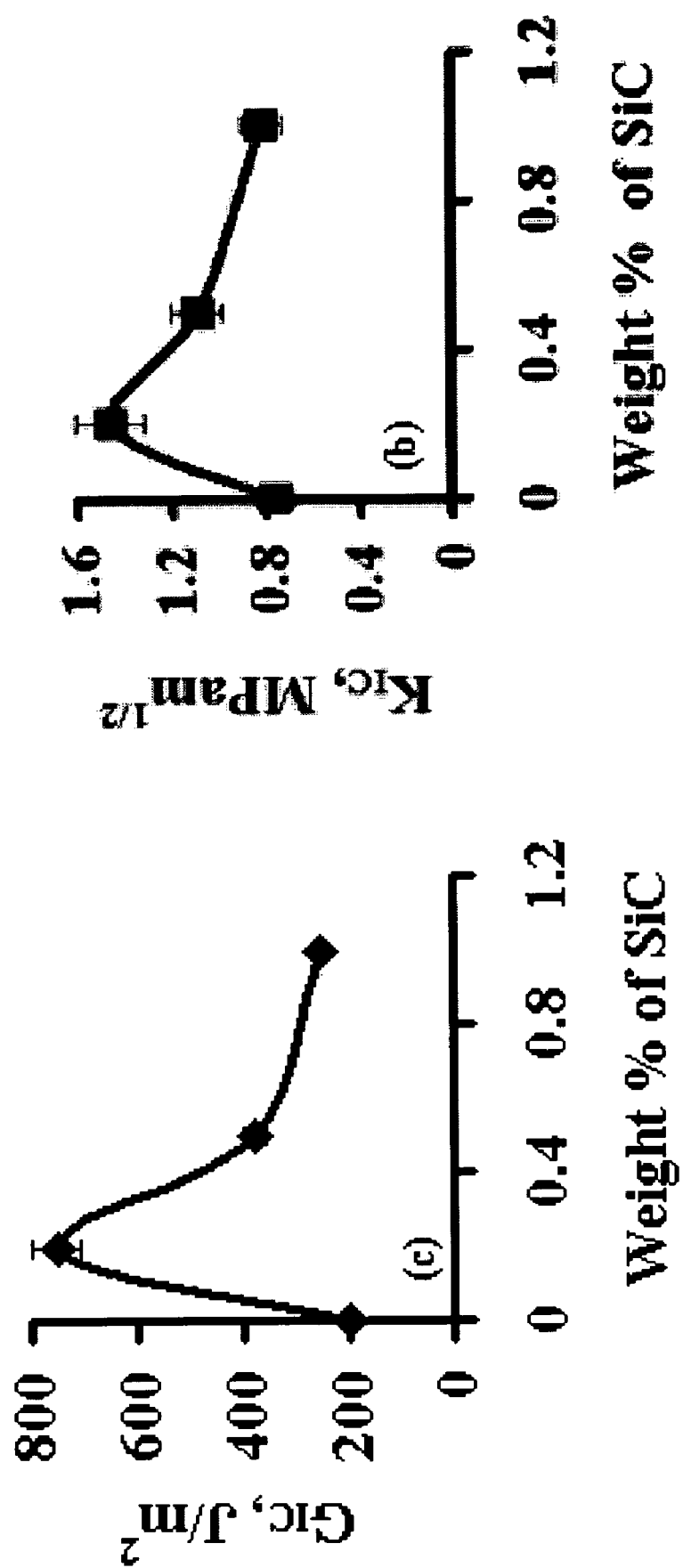
FIGS. 7A-B present the measured fracture properties for SiC nanocomposites and the corresponding neat matrix: (7A) $G_{IC}$ as a function of SiC loading; (6B) $K_{IC}$ as a function of SiC loading.

$K_{IC}$, and $G_{IC}$ values for the nanocomposites and neat matrix as a function of nanoparticle loading are presented in FIGS. 7A-B. In general, improvements in both $K_{IC}$, and $G_{IC}$ values are observed with nanoparticle loadings up to 0.2%. $K_{IC}$ rises from approximately 0.8 MPa m$^{1/2}$ in the neat matrix to approximately 1.5 MPa m$^{1/2}$ in the 0.2%-SiC nanocomposite, a nearly two-fold rise. Similarly, $G_{IC}$ increases from approximately 200 J/m$^2$ to 750 J/m$^2$, over the same range, a nearly four-fold rise. Beyond approximately 0.2% nanoparticle inclusion, both $K_{IC}$ and $G_{IC}$ are found to fall back to approximately the value of the neat matrix. Fracture tests, therefore, demonstrate that significant improvements in the fracture toughness and critical strain energy release rate of epoxy can be obtained with low loadings of nanoparticles, particularly less than approximately 0.2%. In one embodiment, any suitable nanoparticle loading that causes about a two fold or more rise in $G_{IC}$, and/or about a 20% or more rise in $K_{IC}$, may be utilized.

Figure 8A:
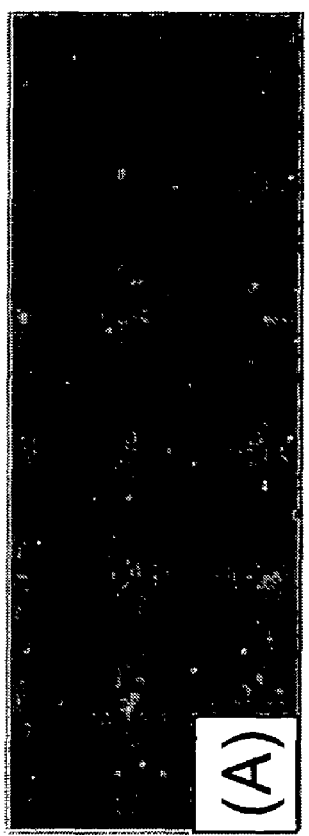
FIGS. 8A-C are micrographs of SENB fracture surfaces of embodiments of a neat matrix (FIG. 8A) and SiC reinforced nanocomposites having loading fractions of 0.2% (FIG. 8B) and 1% (FIG. 8C)
Figure 8B:
Figure 8C:

These mechanical measurements are further supported by SEM micrographs of the fracture surfaces of the two composites, FIGS. 8A-C. The micrograph of the neat epoxy surface (FIG. 8A) shows a very shiny or glossy surface suggesting that brittle, fast propagation of fracture has taken place. The fracture surface of 0.2% SiC reinforced specimen, FIG. 8B) in contrast, is duller. Taken with the mechanical measurements, particularly the stress-strain curves demonstrating plastic yielding, this result illustrates that a more ductile or damage tolerant failure process has occurred in this nanocomposite than in the neat matrix. Furthermore, the fracture surface possesses a very uniform appearance, indicating a lack of agglomerated nanoparticles which would otherwise act as failure initiation sites. Examining the fracture surface of the nanocomposite containing 1% SiC nanoparticles, FIG. 8C, the surface appears non-uniform, with dark, generally circular irregularities of agglomerated SiC particles 242. The micrograph further illustrates striations 802 in the fracture surface, consistent with what would be expected from brittle fracture. Thus at increased nanoparticle concentrations, nanoparticle dispersion becomes more difficult to achieve, resulting in agglomerates 242 which act as defects and striations 802 or stress concentration sites which promote crack propagation and give rise to brittle fracture of nanocomposites.

These mechanical testing and microscopy results demonstrate that low loading fractions of SiC nanoparticles provide composites with substantially dispersed reinforcement having improved toughness, tensile strength, and strain to failure.

Bulk Nanocomposites: $TiO_2$ Nanoparticle Reinforced Nanocomposites

Investigations below illustrate the effects of low loadings of $TiO_2$ nanoparticles on the tensile and fracture properties of nanocomposites and comparable un-reinforced neat matrices. Polyester resin is mixed with $TiO_2$ nanoparticles (Accumet Materials Co.). The $TiO_2$ nanoparticles possess a density of about 0.04-0.06 g/cm$^3$, a surface area of 190-290 m$^2$/g, and a size of approximately 15 nm. $TiO_2$ loadings of 0.2% are investigated in relation to neat polyester matrix only materials. It will be appreciated that other $TiO_2$ loadings may also be utilized, such as in the range of approximately 0.1% to 0.5%. The $TiO_2$ nanoparticles are added to the polyester resin and the mixture stirred using the magnetic mixer approximately 15 hours at 700 rpm in order to disperse the nanoparticles within the matrix resin. Subsequently, the hardener is added to the homogeneous mixture, in an amount so as to provide an epoxy to hardener ratio of approximately 30 mL to 10 drops. Following addition of the hardener, the mixture is stirred manually for approximately 5 minutes at a linear speed of about 1 cm/sec. Following mixing, the mixture is poured into a polished aluminum mold and allowed to cure in air at room temperature for approximately 4 hours. To quantify the effect of the nanoparticles loading on the performance of the composite, a polyester panel without nanoparticles is also manufactured using the same procedure.

Figure 9A:
FIGS. 9A-B are micrographs of embodiments of an as-processed neat matrix and a 0.2% $TiO_2$-reinforced nanocomposite.
Figure 9B:
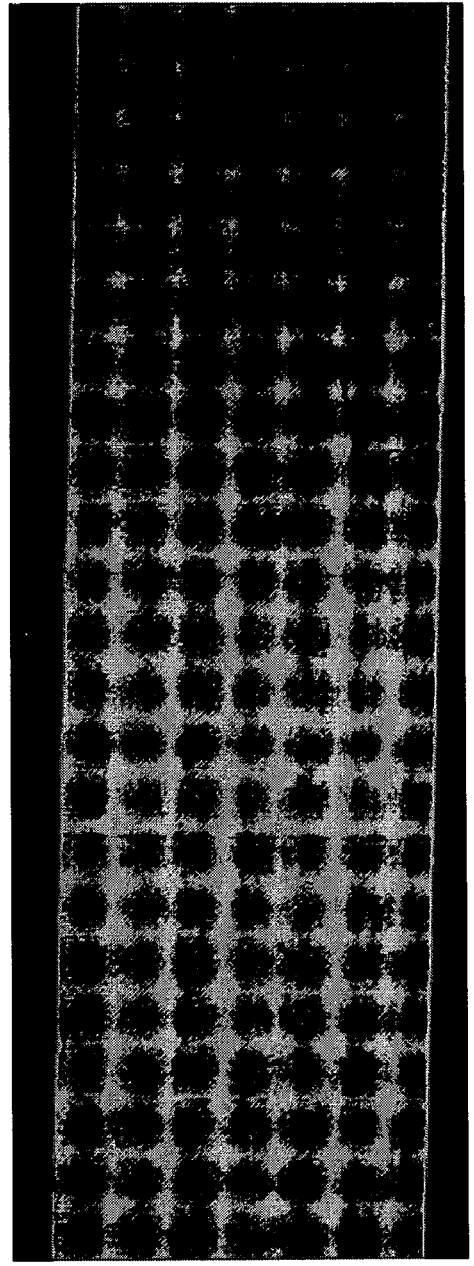

FIGS. 9A-B illustrate the appearance of an as-processed neat matrix (9A) and a 0.2% $TiO_2$-reinforced nanocomposite (9B). It is apparent from the micrographs that the nanocomposite presents a white, opaque appearance, while the neat matrix is approximately transparent. In one aspect, this result demonstrates that even small loadings of nanoparticles are sufficient to change the optical properties of the nanocomposite from those of the neat matrix. In another aspect, this result indicates that the mixing procedure described above provides substantially homogeneous dispersion of the nanoparticles within the resin, as the appearance of the nanocomposite is approximately uniform.

Dogboned tensile specimens were employed for measurement of the tensile properties of the two materials using ASTM D638. At least four specimens were tested for each material condition. FIGS. 10A-C below present the tensile properties of embodiments of the $TiO_2$-Polyester nanocomposites and corresponding neat matrix.

Examining representative stress-strain curves for the nanocomposite, as well as the neat matrix, FIG. 10A, the un-reinforced neat matrix is observed to fail in a brittle manner, with the stress-strain curve rising linearly to failure. In contrast, nanocomposites containing 0.2% $TiO_2$ nanoparticles exhibit yielding prior to failure, as illustrated by the non-linear portion of the curves at elevated values of stress.

FIGS. 10B-C presents the ultimate strength and strain to failure of the $TiO_2$-polyester nanocomposites containing 0.2% $TiO_2$ compared to the baseline neat polyester matrix as well as the relative percentage change in the nanocomposite properties with respect to the baseline. In general, the ultimate strength and strain to failure of the nanocomposites are substantially higher than that obtained in the neat matrix. Specifically, the ultimate strength of the nanocomposite is approximately 25% higher than the neat matrix, approximately 47.43±3.2 MPa, compared to approximately 38±0.05 MPa. Furthermore, the failure strain is almost doubled, from about 0.014±0.001 in the neat matrix to approximately 0.028±0.004 in the 0.02-$TiO_2$ nanocomposite. In other embodiments, any suitable nanoparticle loading that causes an increase in ultimate strength of about 10% or more, or an increase in strain to failure of about 50% or more, may be utilized. Addition of nanoparticles to the neat matrix is found to not significantly affect the Young's modulus of the nanocomposite (about 10% reduction), with the modulus of the neat matrix determined to be approximately 3.15±0.02 GPa to the 2.83±0.4 GPa measured in the nanocomposite.

Figures 11A, 11B:
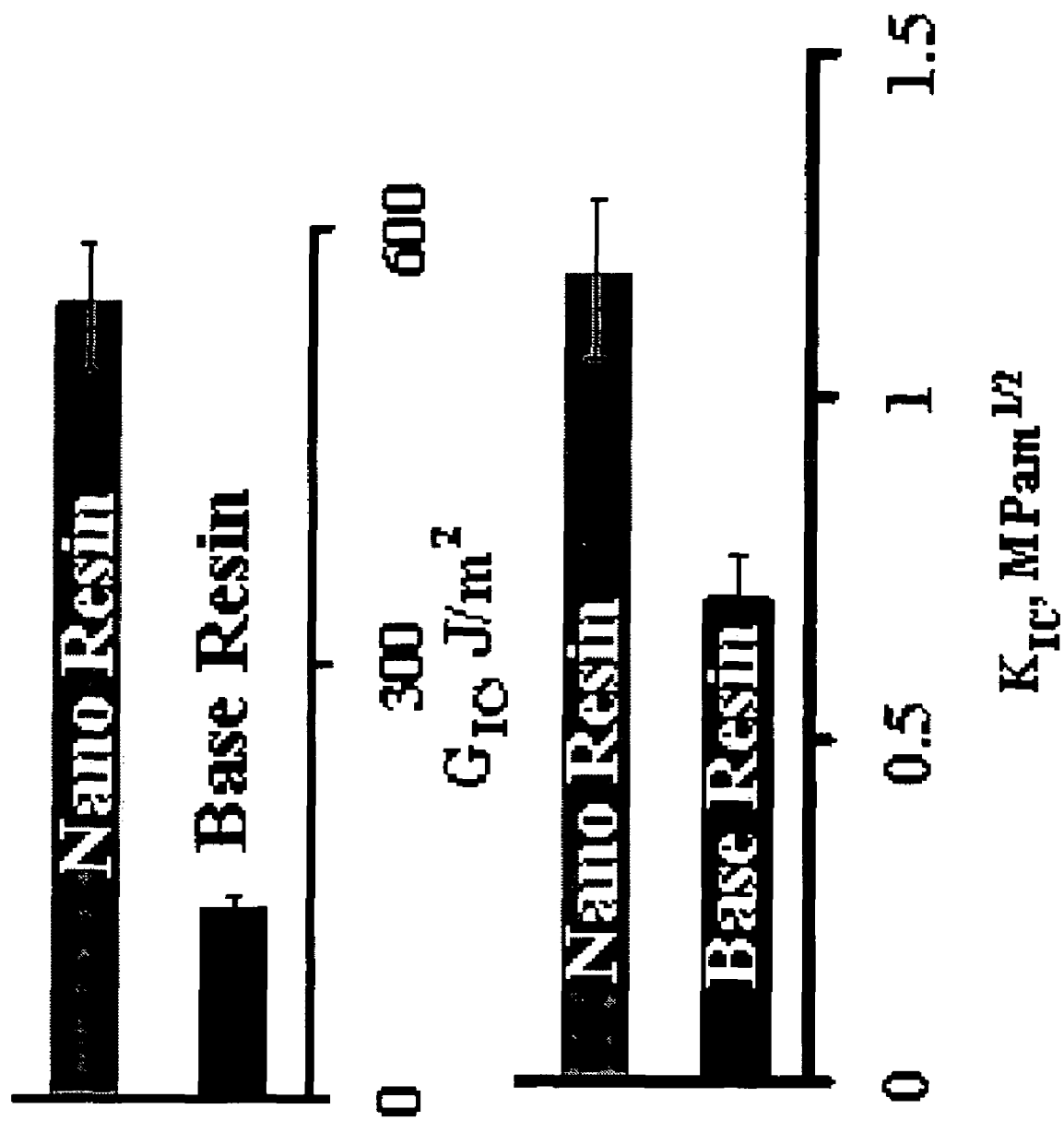
FIGS. 11A-B present measured fracture properties for embodiments of a $TiO_2$ nanocomposites and the corresponding neat matrix; (11A) $G_{IC}$ as a function of $TiO_2$ loading; (11B) $K_{IC}$ as a function of $TiO_2$ loading.

SENB fracture specimens 304 of $TiO_2$ reinforced nanocomposites are provided as schematically illustrated in FIG. 3B. In one embodiment, the fracture specimen 304 has a nominal width of about 12.5 mm, a span length of about 56 mm, and an average thickness of approximately 3.2 mm. A notch 306 of approximately 6 mm in length and 1.5 mm in width is cut using a milling cutter and sharpened using a razor blade tapped into the notch. The SENB specimens 304 so provided have a nominal crack length to specimen width ratio a/W, of approximately 0.5, satisfying the ASTM standard's requirement for a valid SENB test. At least four such specimens were tested for each material condition FIGS. 11A-B illustrate the results of SENB fracture tests of an embodiment of a 0.2% $TiO_2$-polyester nanocomposites and comparable neat polyester matrix. With introduction of the 0.2% $TiO_2$, $K_{IC}$ of the nanocomposite increases from about 0.7 MPa m$^{1/2}$ to about 1.17 MPa m$^{1/2}$, a roughly 65% increase and more than about a 50% increase over the neat matrix. Further, $G_{IC}$ of the nanocomposite increases more than three fold, from approximately 129 J/m$^2$ for the neat matrix to approximately 546 J/m$^2$ for the nanocomposite. In other embodiments, any suitable nanoparticle loading that causes about a two fold or more rise in $G_{IC}$, and/or about a 20% or more rise in $K_{IC}$, may be utilized.

Bulk Nanocomposites: CNT Reinforced Nanocomposites

Investigations below illustrate the effect of inclusion of low loadings of SWNTs on the tensile and fracture properties of nanocomposites and comparable un-reinforced neat polymers. An epoxy based on DGEPBA-AE is mixed with single walled CNTs (SWNTs) (CarboLex Corporation). These carbon nanotubes have an average diameter of approximately 1.4 nm and are found in "ropes" which are typically about 20 nm in diameter or approximately 50 tubes per rope with lengths of 2-5 microns. Two weight fractions of CNTs are investigated: 0.02, and 0.1 wt %. Owing to the high degree of adhesion between nanotubes, SWNTs are difficult to separate into single units from aggregates and clusters within epoxy, as epoxy possesses a high viscosity. To circumvent this difficulty, SWNTs are first dispersed within ethyl alcohol (EtOH).

The nanotubes are added to EtOH and subjected to a sonication treatment for approximately 5 hours at room temperature. The dispersed EtOH-SWNT solution is mixed at room temperature with the resin using a magnetic hot plate stirrer at approximately 700 rpm for about 15 hours. Further stirring at approximately the same speed is continued, in addition to heating at a constant temperature of about 80° C., for about 45 minutes in order to evaporate the highly volatile EtOH from resin. The mixture is subsequently subjected to a second sonication treatment for approximately 25 min. The hardener is then added to the nanotube-epoxy mixture in an approximately 3:1 ratio of epoxy-to-hardener. Subsequently, the nanotube-epoxy-hardener mixture is subjected to slow manual stirring for about 20-30 minutes at a linear speed of approximately 1 cm/sec. This mixing process provides a substantially homogeneously dispersed mixture of SWNT and resin. Following mixing, the mixture is poured into a polished aluminum mold and allowed to cure in air at room temperature for approximately 5 hours. Subsequently, the cured composites are post-cured at approximately 120° C. for 1 hour in air. To quantify the effect of nanotube loading on the performance of the composite, an epoxy panel without nanotubes is also manufactured using the same procedure.

Figure 12A:
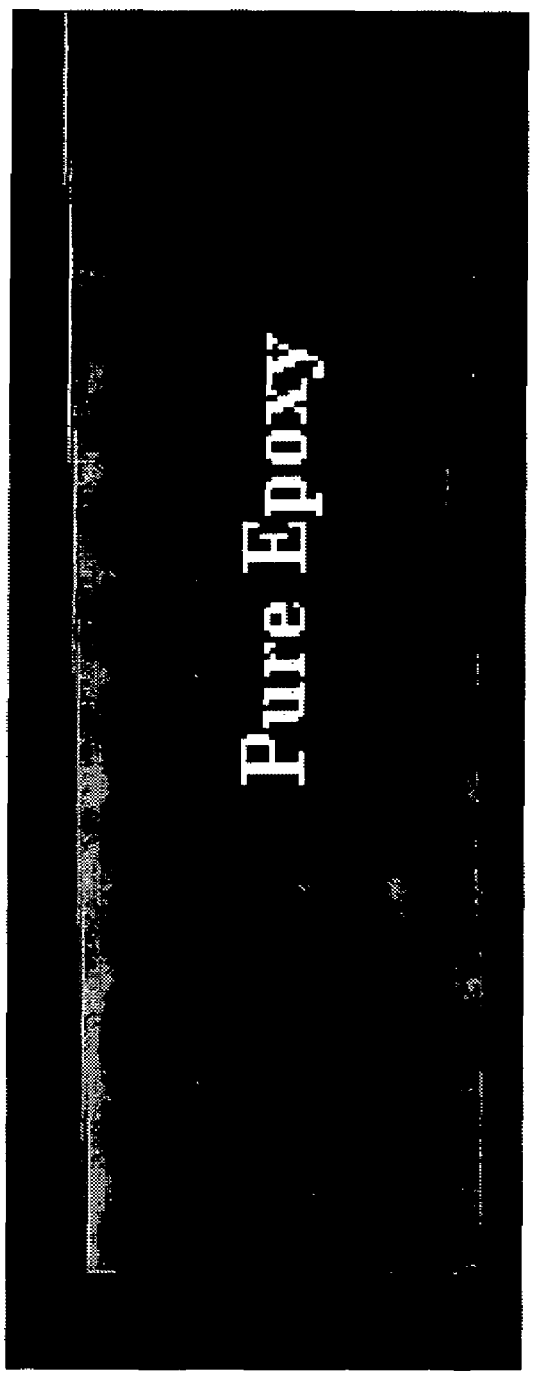
FIGS. 12A-B are photographs of embodiments of an as-processed neat matrix and an approximately 0.02 wt % nanotube-reinforced nanocomposite.
Figure 12B:
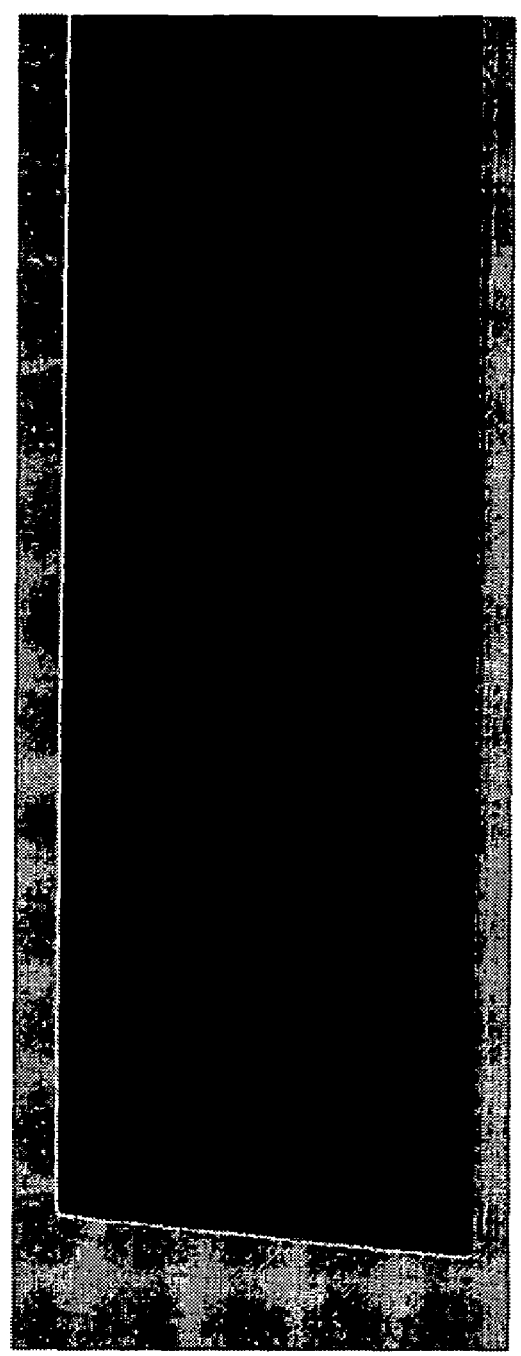

FIGS. 12A-B illustrate the appearance of the as-processed neat matrix and an approximately 0.02% nanotube-reinforced nanocomposite. It is apparent from the micrographs of FIG. 12B, the nanocomposite is colored in appearance, while the neat matrix is approximately transparent, FIG. 12A. In one aspect, this result demonstrates that even small loadings of nanoparticles are sufficient to change the optical properties of the nanocomposite from those of the neat matrix to translucent or opaque. In another aspect, this result indicates that the mixing procedure described above provides substantially homogeneous dispersion of the nanoparticles within the resin, as the appearance of the nanocomposite is approximately uniform.

Dogboned tensile specimens were employed for measurement of the tensile properties of the two materials using ASTM D638. At least four specimens were tested for each material condition. FIGS. 13A-C below present the tensile properties of the CNT-DGEBPA-AE nanocomposites and corresponding neat matrix.

Examining representative stress-strain curves for the nanocomposite, as well as the neat matrix, FIG. 13A, the un-reinforced neat matrix is observed to fail in a brittle manner, with the stress-strain curve rising linearly to failure. In contrast, nanocomposites containing 0.2% CNTs nanoparticles exhibit yielding prior to failure, as illustrated by the non-linear portion of the curves at elevated values of stress FIGS. 13B-C presents the ultimate strength and strain to failure of embodiments of the CNT-DGEBPA-AE nanocomposites containing about 0.02%-0.1% CNTs compared to the baseline neat matrix as well as the relative percentage change in the nanocomposite properties with respect to the baseline.

As illustrated in FIGS. 13B-C, the neat matrix exhibits a brittle elastic response, with the stress-strain response rising approximately linearly to failure. In contrast, the nanotube-reinforced nanocomposites illustrate yielding prior to failure. Furthermore, the ultimate strength and strain to failure of the nanocomposites are higher than that obtained in the neat matrix: ultimate strength of the nanocomposite is approximately 15% higher than the neat matrix, approximately 40.72±4.5 MPa, compared to 35.9±1.05 MPa. The failure strain also illustrates improvement, rising approximately 150% higher to 2.77%, compared to 1.09%. In other embodiments, any suitable nanotube loading that causes an increase in ultimate strength of about 10% or more, and/or an increase in strain to failure of about 50% or more, may be utilized. The Young's modulus of the nanocomposite is found to be reduced approximately 45%, with the modulus of the neat matrix measured to be approximately 3.5 GPa to the 2.04 GPa measured in the nanocomposite.

SENB fracture specimens 304 of CNT reinforced nanocomposites are provided as schematically illustrated in FIG. 3B. The SENB specimens 304 tested possess a width of approximately 12.5 mm, a span length of approximately 56 mm, and an average thickness of approximately 3.2 mm. A notch 306 of approximately 6 mm in length and 1.5 mm width is cut into the specimens using a milling cutter and sharpened using a razor blade tapped into the notch. So configured, the crack length to width ratio, a/W, is approximately 0.5, satisfying the ASTM requirements for a valid SENB fracture test.

Figures 14A, 14B:
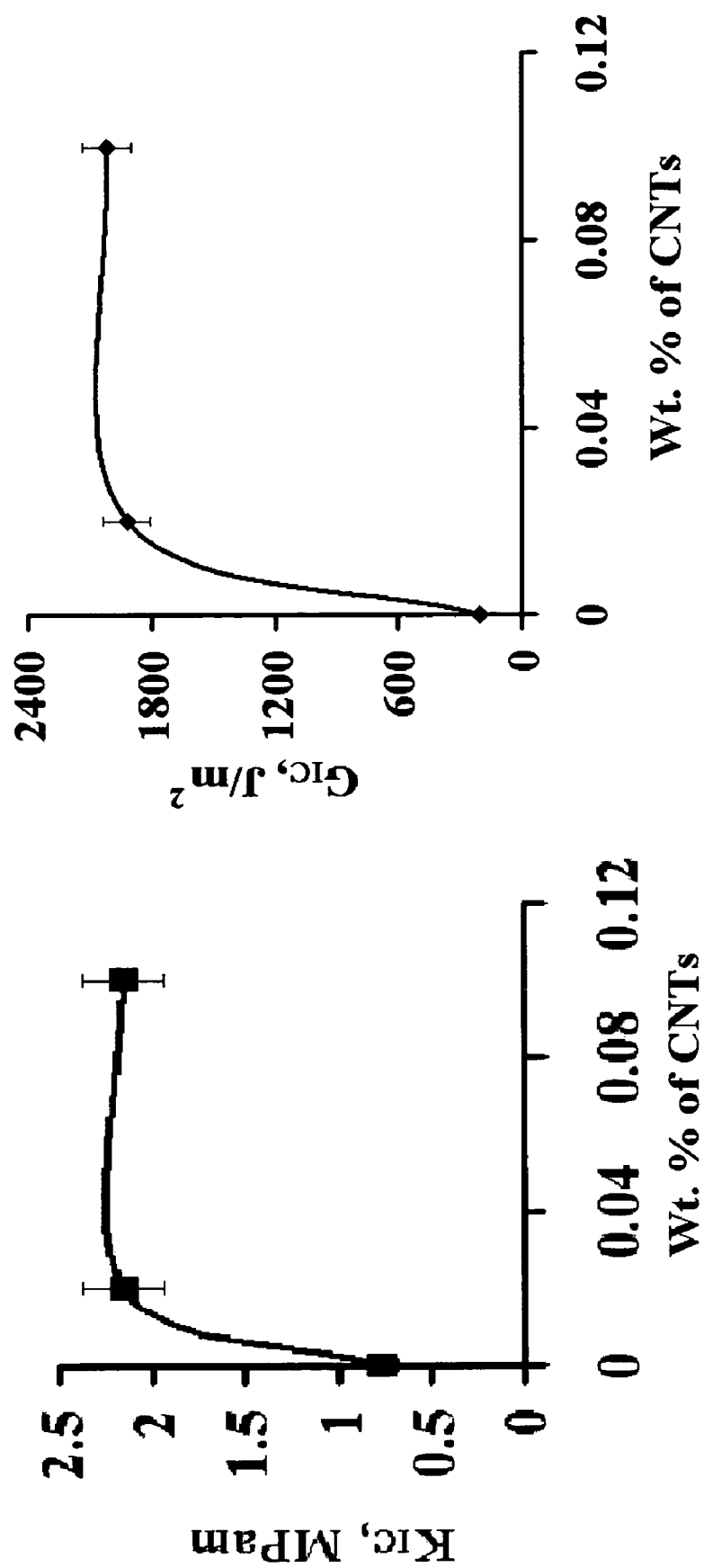
FIGS. 14A-B present measured fracture properties for embodiments of CNT nanocomposites and the corresponding neat matrix: (14A) $K_{IC}$ as a function of CNT loading; (14B) $G_{IC}$ as a function of CNT loading.

FIG. 14A-B illustrates the results of SENB fracture tests of embodiments of nanotube-epoxy nanocomposites and the neat matrix. With introduction of the 0.02-0.1% nanotubes, $K_{IC}$ of the nanocomposite more than doubled, exhibiting a roughly three fold increase, from about 0.7 MPa m$^{1/2}$ in the neat matrix, to about 2.2 MPa m$^{1/2}$ in the nanocomposite. Further, $G_{IC}$ of the nanocomposite increases by more than a factor of 8 and almost ten fold over the neat matrix, from approximately 200 J/m$^2$ for the neat matrix to approximately 1900 J/m$^2$ for the nanocomposite.

EXAMPLES

Nanocomposite Coatings

In further examples, testing is also performed on polymer coatings reinforced using nanoparticles and their corresponding un-reinforced counterparts in order to illustrate the property improvements which may be achieved in these coatings over un-reinforced coatings. In the examples below, polymer coatings comprising nail polish are investigated. In particular, chemical resistance and mechanical resistance to wear and chipping are examined. While the examples below illustrate nail polishes reinforced with TiO$_2$ nanoparticles, it may be understood that other nanoparticles which include, but are not limited to SiC, ZnO, Y$_2$O$_3$, and C, as well as CNTs may be utilized in alternative embodiments of the invention. In preferred embodiments of the invention, a single nanoparticles or nanotubes species is provided as a reinforcement.

In general, when applying nail polish, three coatings are employed, a base coating which is applied directly upon the nail, a main color coating which is applied upon the base coating, and a top coating which is applied upon the main color. To test the influence of nanoparticle reinforcements on nail polish coatings, representative, commercially available nail polish products are employed. For example, base and top coatings comprising REVLON® FIRMA NAIL and main color coatings comprising REVLON® COLOR ILLUSION, having a metallic red color, are examined. REVLON® FIRMA NAIL comprises combinations of the following compounds: Isopropanol, Acetyl tributyl citrate, Citric acid, Butyl acetate, Sucrose acetate isobutyrate, Ethyl acetate, Heptane, Etocrylene, Malic acid, Bismuth oxychloride, Nitrocellulose, Sucrose benzoate, 2-Propenoic acid, polymer with N-(1,1-dimethylethyl)-2-propenamide and ethyl 2-propenoate, Stearalkonium hectorite, and Stearalkonium bentonite. REVLON® COLOR ILLUSION, is a nail enamel, generally comprising film forming agents (e.g. Nitrocellulose), resins and plasticizers, solvents, and coloring agents. Further details regarding the formulation of nail polish utilized in embodiments of the invention discussed above may be found in U.S. Patent Application Publication 2005/0220730 to Malnou, et al., the entirety of which is hereby incorporated by reference.

Sample Preparation: Nanocomposite Coatings $TiO_2$ nanoparticles are added to each nail polish coating separately and dispersed using the magnetic stirring technique discussed above. The $TiO_2$ nanoparticles possess a particle size of approximately 15 nm, a density in the range of about 0.04-0.06 g/cm$^3$, and a surface area of approximately 190-290 m$^2$/g. Preferably, the nanoparticles may be provided in a quantity as described above, for example about 0.1 wt % to 0.4 wt %, more preferably about 0.2 wt %. To distribute the nanoparticles uniformly within the coatings, an octagonal stirring bar having a length of approximately ½ inch and a diameter of approximately ⅛ inch is used for magnetic stirring. Stirring is performed in a closed container at a speed in the range of about 220-280 r.p.m. for approximately 15 hours.

Examining the as-mixed coatings, several observations were noted. In one aspect, after mixing, it is observed that the main color is substantially unchanged by the nanoparticle reinforcement. In another aspect, the color of the base and top coatings exhibited modest whitening. It is further noted, however, that the change in color of the base and top coatings did not substantially alter the appearance of the final nail polish color when the three coatings were layered upon one another. While nanoparticle reinforcements of nail polishes have previously been performed, such as in U.S. patent application No. 2005/0220730, the influence of the reinforcement on the color of the resulting polish has not previously been appreciated. In embodiments of the present invention, the loading fraction of the nanomaterial reinforcement is selected so as to not substantially influence the color of the resulting polish. It is additionally noted that the nanoparticle reinforcement had substantially no influence on the consistency of the nail polish or ease of application.

with nanoparticles and two sets using unreinforced nail polish. Each set possessed three nails.

In the second configuration, one layer of base coating, two layers of main color coating, and one layer of top coating are applied, while the layers which possess the nanoparticle reinforcement are varied. A drying time of approximately 10 minutes is employed after each coating layer is applied. In a first sample set, each coating is without nanoparticle reinforcement. In a second sample set, only the base layer possesses the nanoparticle reinforcement. In a third sample set, the base coating and the two main color coating layers possess the nanoparticle reinforcement. In a fourth sample set, the nanoparticle reinforcement is present within all the coating layers. Nails prepared in this manner are observed to demonstrate substantially no difference in appearance, despite the variation in nanoparticle reinforcement.

In preparation for testing, the coated nails are glued to aluminum bars having diameters and curvatures approximately equal to that of the nails. Approximately ⅔ of the length of each nail, about 12.5 mm, is affixed to the aluminum bars, leaving about ⅓ of the nail length, or approximately 6.5 mm, extending past the end of the bars.

Chemical and Mechanical Testing: Nanocomposite Coatings

To examine the performance of nanoparticle reinforced nail polish, chemical and mechanical tests are performed to simulate environments and activities that human nails are commonly exposed to and engaged in. Chemical tests are performed by soaking the prepared nails in common household chemicals. A concentration of approximately 50 wt % is used for all chemicals in order to provide a relatively conservative simulation of chemical exposure. Mechanical testing is performed by simulating a typing action. The aluminum bars are used as fingers to cyclically press the nail tips into and out of contact with a computer keyboard. The testing times are illustrated in Table II below.

TABLE II

| | | Testing Matrix | | | |
|---|---|---|---|---|---|
| Test | Brand | Concentration (wt %) | Daily Exposure Time (min) | Life Cycle Exposure Time (h) | Time/Cycle (min) |
| Chemical | | | | | |
| Dish Washing Liquid | Dawn ® | 50 | 48 | 22.5 | 150 |
| Liquid Hand Soap | Ivory ® | | 16 | 7.5 | 50 |
| Hair Shampoo | Suave ® | | 13 | 6 | 40 |
| Hair Conditioner | Suave ® | | 6.5 | 3 | 20 |
| Makeup Remover | Neutrogena Deepclean ® | | 1.5 | 0.75 | 5 |
| | | | TOTAL 85 | TOTAL 39.75 | TOTAL 265 (4.42 h) |
| Mechanical | | | | | |
| Typing | | | TOTAL 19 | TOTAL 9 | 60 (1 h) |

The prepared coatings are applied to artificial finger nails for testing. A commercially available artificial nail, Fing'rs®, is employed. These artificial nails possess a length of approximately 19 mm and a curvature of about 6.5 mm. The coatings are applied to the nails using appropriate nail polish brushes in two different configurations. In the first configuration, a layer of either the base coating/top coating or the main coating is applied to the nail. Four sets of nails are coated in this manner for testing, with two sets using nail polish reinforced Chemical and mechanical tests to evaluate the performance of nanoparticle reinforced nail polish are conducted on the polished nails based upon an estimation of a daily exposure time for each chemical or mechanical activity (typing). Respectively, the daily exposure times are taken to be approximately 48, 16, 13, 6.5, and 1.5 minutes for dish washing liquid, liquid hand soap, hair shampoo, hair conditioner, and makeup remover. Similarly, the daily time spent typing is taken to be approximately 19 minutes.

The daily exposure time is used to estimate the total exposure time over the life cycle of the nail polish. Taking the life cycle of the nails to be approximately four weeks, the daily exposure time is multiplied by 28 days to yield approximate values for the total exposure time over the life cycle of the present nails. These values are taken to be, respectively, 22.5, 7.5, 6, 3, and 0.75 hours for dish washing liquid, liquid hand soap, hair shampoo, hair conditioner, and makeup remover.

Accelerated testing is performed to simulate these total exposure times. The total exposure time for each chemical and mechanical activity is divided into 9 testing cycles. In a cycle, the nails are successively soaked in dish washing liquid, liquid hand soap, hair shampoo, hair conditioner, and makeup remover, for approximately 150, 50, 40, 20, and 5 minutes, respectively. Between each exposure, the nails are allowed to dry for approximately 2 hours. Nails are wiped and dried after each chemical exposure using paper towels for the last five testing cycles. Following each chemical exposure cycle, the nails are used to type continuously for approximately one hour, cyclically bringing the nails in and out of contact with a keyboard in order to simulate a typing action on a computer keyboard. Upon completion of all the testing cycles, the appearance of the nails is examined.

Examination and comparison of the nails having single layer nanocomposite coatings, multiple layer nanocomposite coatings, and their unreinforced counterparts revealed that nail polishes with nanoparticle reinforcements often exhibit superior performance to unreinforced nail polishes. FIG. 15A-B illustrates artificial nails 1500 having a single layer of main color coating which are unreinforced (FIG. 15A) and reinforced with the $TiO_2$ nanoparticles (FIG. 15B). It is observed that the unreinforced nail polish exhibits scratches 1502 on the surface of the nail after testing, as well as chipping 1504 at the tip of the nail. In contrast, nails painted with nanoparticle reinforced nail polish appear substantially free of such scratching or chipping. These results, therefore, demonstrate that the nanoparticle reinforcement enhances the durability, and thus the useful lifetime, of single nail polish coatings.

And while the single layer main color coatings tested using the techniques, setup, and durations discussed above showed clear differences in terms of scratches and chipping with and without nanoparticles, the multiple layer nail polish coatings with and without nanoparticles did not illustrate such differences. Further testing may be required to clearly identify improvements.

These findings demonstrate the substantial gains which can be achieved in strength and strain to failure, as well as in toughening upon low percentage reinforcement of bulk polymer matrices with homogenously distributed nanoparticles and nanotubes. The results further show that nail polish applications may benefit from the use of low loading fractions of reinforcing nanoparticles. It should be noted that U.S Patent Application Publication 2005/0220730 fails to appreciate the advantages and features which may be obtained in nail polishes and other polymer systems reinforced with nanomaterials in the quantities and to obtain the properties as discussed above, and for example in the loading range of approximately 0.01 to 0.4 wt %. In particular, the benefits to the strength and toughness of nanocomposites so reinforced have not previously been recognized.

Thus, certain embodiments of the present invention provide systems and methods of fabricating nanocomposites having low weight fractions of nanoparticles and nanotubes which are substantially uniformly distributed. Advantageously, the disclosed mixing technique, including a magnetic mixing step, provide a substantially uniform distribution of the nanotubes and nanoparticles which can provide significantly enhanced tensile strength, strain to failure, and fracture toughness over neat matrices alone.

Although the foregoing description has shown, described, and pointed out the fundamental novel features of the present teachings, it will be understood that various omissions, substitutions, and changes in the form of the detail of the apparatus as illustrated, as well as the uses thereof, may be made by those skilled in the art, without departing from the scope of the present teachings. Consequently, the scope of the present teachings should not be limited to the foregoing discussion, but should be defined by the appended claims.

What is claimed is:

1. A composite material, comprising:
   a matrix material selected from the group consisting of epoxies and polyesters; and
   a reinforcement material comprising at least one of nanoparticles selected from the group consisting of $TiO_2$, ZnO, SiC, $Y_2O_3$, C and carbon nanotubes having at least one dimension of about 100 nm or less dispersed within the matrix material, wherein the reinforcement is present in a concentration between approximately 0.01% and 0.4% on the basis of the weight of the composite material so as to improve at least one of strength and toughness of the composite.

2. A nanomaterial-reinforced nail polish comprising the composite material of claim 1, wherein the reinforcement material is present in a concentration between approximately 0.2 to 0.4 wt %.

3. The composite material of claim 1, wherein the reinforcement material is present in a concentration between approximately 0.1% to 0.4% on the basis of weight of the composite material.

4. The composite material of claim 1, wherein the matrix material comprises an epoxy and the reinforcement material comprises SiC.

5. The composite material of claim 4, wherein the SiC reinforcement material is provided in a concentration between about 0.2% and 0.4% on the basis of the weight of the composite material.

6. The composite material of claim 1, wherein the matrix material comprises a polyester resin and the reinforcement material comprises $TiO_2$.

7. The composite material of claim 6, wherein the $TiO_2$ reinforcement material is provided in a concentration of about 0.2% on the basis of the weight of the composite material.

8. The composite material of claim 1, wherein the reinforcement material comprises carbon nanotubes in a concentration of about 0.01% to 0.1% on the basis of the weight of the composite material.

9. The composite material of claim 1, wherein the matrix comprises a high temperature epoxy based on diglycidyl ether of bisphenol A and alkylglycidyl ether, a ceramic based on a pre-ceramic polymer, or polyester.

10. The composite material of claim 1, wherein the reinforcement causes an increase in ultimate strength of the composite of about 10% or more compared to an unreinforced matrix.

11. The composite material of claim 1, wherein the reinforcement causes an increase in strain to failure of the composite of about 50% or more compared to an unreinforced matrix.

12. The composite material of claim 1, wherein the reinforcement causes an increase in $G_{IC}$ of about two-fold or more compared to an unreinforced matrix.

13. The composite material of claim 1, wherein the reinforcement causes an increase in $K_{IC}$ of about 20% or more compared to an unreinforced matrix.

14. The composite material of claim 1, wherein the matrix material comprises a nail polish and the reinforcement material comprises $TiO_2$.

15. The composite material of claim 14, wherein the $TiO_2$ reinforcement material is provided in a concentration of about 0.2% on the basis of the weight of the composite material.

16. The nail polish of claim 2, wherein color of the nail polish is substantially unchanged by the presence of the reinforcement material.

\* \* \* \* \*

UNITED STATES PATENT AND TRADEMARK OFFICE
CERTIFICATE OF CORRECTION

PATENT NO. : 7,658,870 B2  Page 1 of 1
APPLICATION NO. : 11/524091
DATED : February 9, 2010
INVENTOR(S) : Nejhad et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 549 days.

Signed and Sealed this

Twenty-eighth Day of December, 2010

David J. Kappos
*Director of the United States Patent and Trademark Office*